US009688964B2

(12) United States Patent
Love et al.

(10) Patent No.: US 9,688,964 B2
(45) Date of Patent: Jun. 27, 2017

(54) NANOPARTICLE SYNTHESIS USING PLANT EXTRACTS AND VIRUS

(71) Applicant: THE JAMES HUTTON INSTITUTE, Dundee (GB)

(72) Inventors: Andrew John Love, Dundee (GB); Mikhail Emmanuilovich Talianski, Dundee (GB); Sean Nicholas Chapman, Dundee (GB); Jane Shaw, Denny (GB)

(73) Assignee: THE JAMES HUTTON INSTITUTE, Dundee (GB)

( * ) Notice: Subject to any disclaimer, the term of this patent is extended or adjusted under 35 U.S.C. 154(b) by 0 days.

(21) Appl. No.: 14/429,620

(22) PCT Filed: Sep. 20, 2013

(86) PCT No.: PCT/GB2013/052473
§ 371 (c)(1),
(2) Date: Mar. 19, 2015

(87) PCT Pub. No.: WO2014/045055
PCT Pub. Date: Mar. 27, 2014

(65) Prior Publication Data
US 2015/0218524 A1  Aug. 6, 2015

(30) Foreign Application Priority Data
Sep. 21, 2012  (GB) .................. 1216930.6

(51) Int. Cl.
C12N 7/00  (2006.01)
A61K 9/51  (2006.01)
B82Y 5/00  (2011.01)

(52) U.S. Cl.
CPC .............. C12N 7/00 (2013.01); A61K 9/5123 (2013.01); B82Y 5/00 (2013.01); C12N 2710/20023 (2013.01); C12N 2710/20031 (2013.01); C12N 2770/00023 (2013.01); C12N 2770/00031 (2013.01); C12N 2770/18023 (2013.01); C12N 2770/18031 (2013.01); C12N 2770/34023 (2013.01); C12N 2770/34031 (2013.01); C12N 2770/40023 (2013.01); C12N 2770/40031 (2013.01)

(58) Field of Classification Search
None
See application file for complete search history.

(56) References Cited

U.S. PATENT DOCUMENTS

| 8,333,994 | B2 * | 12/2012 | Katti | A61K 9/148 |
| | | | | 424/489 |
| 2015/0218524 | A1 * | 8/2015 | Love | C12N 7/00 |
| | | | | 424/490 |

OTHER PUBLICATIONS

Kadri et al. (Virus Research. 2011; 157 (1): 35-46).*
Wang, Jing; "Electrochemical Biosensing based on Noble Metal Nanoparticles"; Microchim Acta, vol. 177; Jan. 13, 2012; pp. 245-270.
Lonnoy, Olivier; "International Search Report" for PCT/GB2013/052473 as mailed Dec. 20, 2013; 3 pages.
Kadri, A., et al.; "Engineered Tobacco Mosaic Virus Mutants with Distinct Physical Characteristics in planta and Enhanced Metallization Properties"; Virus Research, vol. 157, No. 1; Jan. 29, 2011; pp. 35-46.
Gan, Pei Pei, et al.; "Potential of Plant as a Biological Factory to Synthesize Gold and Silver Nanoparticles and their Applications"; Rev Environ Sci Biotechnol, vol. 11, No. 2; Apr. 10, 2012; pp. 169-206.
Raveendran, P., et al.; "Completely 'Green' Synthesis and Stabilization of Metal Nanoparticles"; Journal of the American Chemical Society, vol. 125, No. 46; Nov. 8, 2002; pp. 13940-13941.
Aljabali, A.A.A., et al.; "Virus Templated Metallic Nanoparticles"; Nanoscale, vol. 2, No. 12; Jan. 1, 2010; pp. 2596-2600.
Balci, S., et al.; "Copper Nanowires within the Central Channel of Tobacco Mosaic Virus Particles"; Electrochimica Acta, vol. 51, No. 28; Sep. 15, 2006; pp. 6251-6257.
Höppener, Christiane, et al.; "Exploiting the Light-Metal Interaction for Biomolecular Sensing and Imaging"; Quarterly Reviews of Biophysics, vol. 45, No. 2; May 3, 2012; pp. 209-255.
Narayanan, Kannan Badri, et al.; "Green Synthesis of Biogenic Metal Nanoparticles by Terrestrial and Aquatic Phototrophic and Heterotrophic Eukaryotes and Biocompatible Agents"; Advances in Colloid and Interface Science, vol. 169; Sep. 8, 2011; pp. 59-79.
Sharma, Virender K., et al.; "Silver Nanoparticles: Green Synthesis and their Antimicrobial Activities"; Advances in Colloid and Interface Science, vol. 145; Sep. 17, 2009; pp. 83-96.
Narayanan, Kannan Badri, et al.; "Biological Synthesis of Metal Nanoparticles by Microbes"; Advances in Colloid and Interface Science, vol. 156; Feb. 10, 2010; pp. 1-13.
Govindaraju, Kasivelu, et al.; "Silver, Gold and Bimetallic Nanoparticles Production using Single-Cell Protein (*Spirulina platensis*) Geitler"; J Matter Sci; Jul. 2008; 8 pages.
Scarano, Gioacchino, et al.; "Characterization of Cadmium- and Lead- Phytochelatin Complexes formed in a Marine Microalga in Response to Metal Exposure"; BioMetals, vol. 15; Nov. 21, 2001; pp. 145-151.
Scarano, Gioacchino, et al.; "Properties of Phytochelatin-Coated CdS Nanocrystallites Formed in a Marine Phytoplanktonic Alga (*Phaeodactylum tricornutum*, Bohlin) in Response to Cd"; Plant Science, vol. 165; Jun. 5, 2003; pp. 803-810.
Anshup et al.; "Growth of Gold Nanoparticles in Human Cells"; Langmuir, vol. 21, No. 25; Nov. 9, 2005; pp. 11562-11567.
Lengke, Maggy F., et al.; "Biosynthesis of Silver Nanoparticles by Filamentous Cyanobacteria from a Silver(I) Nitrate Complex"; Langmuir, vol. 23, No. 5; Jan. 18, 2007; pp. 2694-2699.

(Continued)

Primary Examiner — Shanon A Foley
(74) Attorney, Agent, or Firm — Winstead PC

(57) ABSTRACT

There is described a process for production of metal-coated virus particles or metallic nanoparticles, said process comprising admixing virus particles with plant material with reducing power and a metal salt, wherein the process can be provided in planta or ex planta and the virus particles aid the production of the metal-coated virus particles or metallic nanoparticles.

20 Claims, 8 Drawing Sheets

(56) References Cited

OTHER PUBLICATIONS

Shankar, S. Shiv, et al.; "Bioreduction of Chloroaurate Ions by Geranium Leaves and its Endophytic Fungus yields Gold Nanoparticles of different Shapes"; J. Matter Chem., vol. 13; May 27, 2003; pp. 1822-1826.

Shankar, S. Shiv, et al.; "Biological Synthesis of Triangular Gold Nanoprisms"; Nature Materials, vol. 3; Jun. 20, 2004; pp. 482-488.

Shankar, S. Shiv, et al.; "Rapid Synthesis of Au, Ag, and Bimetallic Au Core-Ag Shell Nanoparticles using Neem (*Azadirachta indica*) Leaf Broth"; Journal of Colloid and Interface Science, vol. 275; Apr. 9, 2004; pp. 496-502.

Maensiri, S., et al.; "Indium Oxide ($In_2O_3$) Nanoparticles using *Aloe vera* Plant Extract: Synthesis and Optical Properties"; Optoelectronics and Advanced Materials—Rapid Communications, vol. 2, No. 3; Mar. 2008; pp. 161-165.

Vilchis-Nestor, Alfredo R., et al.; "Solventless Synthesis and Optical Properties of Au and Ag Nanoparticles using *Camellia sinensis* Extract"; Materials Letters, vol. 62; Feb. 19, 2008; pp. 3103-3105.

Song, Jae Yong, et al.; "Rapid Biological Synthesis of Silver Nanoparticles using Plant Leaf Extracts"; Bioprocess Biosyst Eng, vol. 32; Apr. 26, 2008; pp. 79-84.

Balci, Sinan, et al.; "Electroless Synthesis of 3nm wide Alloy Nanowires inside Tobacco mosaic virus"; Nanotechnology, vol. 23; Jan. 4, 2012; 7 pages.

Knez, Mato, et al.; "Atomic Layer Deposition on Biological Macromolecules: Metal Oxide Coating of Tobacco Mosaic Virus and Ferritin"; Nano Letters, vol. 6, No. 6; Apr. 27, 2006; pp. 1172-1177.

Endo, Masayuki, et al.; "Pyrene-Stacked Nanostructures Constructed in the Recombinant Tobacco Mosaic Virus Rod Scaffold"; Chem. Eur. J., vol. 12; Feb. 28, 2006; pp. 3735-3740.

Shimizu, Toshimi, et al.; "Supramolecular Nanotube Architectures Based on Amphiphilic Molecules"; Chem. Rev., vol. 105; Mar. 24, 2005; pp. 1401-1443.

Lee, Sang-Yup, et al.; "Synthesis and Application of Virus-Based Hybrid Nanomaterials"; Biotechnology and Bioengineering, vol. 109, No. 1; Sep. 13, 2011; pp. 16-30.

Bittner, Alexander M.; "Biomolecular Rods and Tubes in Nanotechnology"; Naturwissenschaften, vol. 92; Nov. 19, 2004; pp. 51-64.

Dujardin, Erik, et al.; "Organization of Metallic Nanoparticles using Tobacco Mosaic Virus Templates"; Nano Letters, vol. 3, No. 3; Feb. 12, 2003; pp. 413-417.

Atanasova, Petia, et al.; "Virus-Templated Synthesis of ZnO Nanostructures and Formation of Field-Effect Transistors"; Advanced Materials, vol. 23; Sep. 30, 2011; pp. 4918-4922.

Chen, Xilin, et al.; "High Rate Performance of Virus Enabled 3D n-Type Si Anodes for Lithium-Ion Batteries"; Electrochimica Acta, vol. 56; Mar. 21, 2011; pp. 5210-5213.

Wu, Zhenyu, et al.; "Enhancing the Magnetoviscosity of Ferrofluids by the Addition of Biological Nanotubes"; ACS Nano, vol. 4, No. 8; Jul. 22, 2010; pp. 4531-4538.

Love, Andrew J., et al.; "In planta Production of a Candidate Vaccine against Bovine Papillomavirus Type 1"; Planta, vol. 236; Jun. 21, 2012; pp. 1305-1313.

Tan, Yen Nee, et al.; "Uncovering the Design Rules for Peptide Synthesis of Metal Nanoparticles"; J. Am. Chem. Soc., vol. 132, No. 16; Mar. 31, 2010; pp. 5677-5686.

Saunders, Keith, et al.; "Efficient Generation of cowpea mosaic virus Empty Virus-Like Particles by the Proteolytic Processing of Precursors in Insect Cells and Plants"; Virology, vol. 393; Sep. 5, 2009; pp. 329-337.

Aljabali, Alaa A. A., et al.; "Chemically-Coupled-Peptide-Promoted Virus Nanoparticle Templated Mineralization"; Integrative Biology, vol. 3, No. 2; Oct. 28, 2010; pp. 119-125.

Lukman, Audra I., et al.; "Facile Synthesis, Stabilization, and Anti-Bacterial Performance of Discrete Ag Nanoparticle using *Medicago sativa* Seed Exudates"; Journal of Colloid and Interface Science, vol. 353; Oct. 25, 2010; pp. 433-444.

Lin, Liqin, et al.; "Nature Factory of Silver Nanowires: Plant-Mediated Synthesis using Broth of *Cassia fistula* Leaf"; Chemical Engineering Journal, vol. 162; Jun. 17, 2010; pp. 852-858.

Das, Ratul Kumar, et al.; "Green Synthesis of Gold Nanoparticles using *Nyctanthes arbortristis* Flower Extract"; Bioprocess Biosyst Eng, vol. 34; Jan. 13, 2011; pp. 615-619.

Thuenemann, Eva C., et al.; "The Use of Transient Expression Systems for the Rapid Production of Virus-Like Particles in Plants"; Current Pharmaceutical Design, vol. 19, No. 31; Jan. 31, 2013; pp. 5564-5573.

Nadagouda, Mallikarjuna N., et al.; "Green Synthesis of Silver and Palladium Nanoparticles at Room Temperature using Coffee and Tea Extract"; Green Chem., vol. 10; Jul. 1, 2008; pp. 859-862.

Nadagouda, Mallikarjuna N., et al.; "In vitro Biocompatibility of Nanoscale Zerovalent Iron Particles (NZVI) Synthesized using Tea Polyphenols"; Green Chem., vol. 12; Nov. 4, 2009; pp. 114-122.

Njagi, Eric C., et al.; "Biosynthesis of Iron and Silver Nanoparticles at Room Temperature using Aqueous Sorghum Bran Extracts"; Langmuir, vol. 27, No. 1; Dec. 6, 2010; pp. 264-271.

Yilmaz, M., et al.; "Biosynthesis of Silver Nanoparticles using Leaves of *Stevie rebaudiana*"; Materials Chemistry and Physics, vol. 130; Aug. 27, 2011; pp. 1195-1202.

Bankar, Ashok, et al.; "Banana Peel Extract Mediated Synthesis of Gold Nanoparticles"; Colloids and Surfaces B: Biointerfaces 80; May 27, 2010; pp. 45-50.

Raghunandan, D., et al.; "Biosynthesis of Stable Polyshaped Gold Nanoparticles from Microwave-Exposed Aqueous Extracellular Anti-Malignant Guava (*Psidium guajava*) Leaf Extract"; Nanobiotechnol, vol. 5; Oct. 6, 2009; pp. 34-41.

Armendariz, Veronica, et al.; "Size Controlled Gold Nanoparticle Formation by *Avena sativa* Biomass: Use of Plants in Nanobiotechnology"; Journal of Nanoparticle Research, vol. 6; May 10, 2004; pp. 377-382.

Dwivedi, Amarendra Dhar, et al.; "Biosynthesis of Silver and Gold Nanoparticles using *Chenopodium album* Leaf Extract"; Colloids and Surfaces A: Physicochem. Eng. Aspects, vol. 369; Jul. 30, 2010; pp. 27-33.

Singh, Ashwani Kumar, et al.; "Biosynthesis of Gold and Silver Nanoparticles by Natural Precursor Clove and their Functionalization with Amine Group"; J Nanopart Res, vol. 12; Jan. 6, 2010; pp. 1667-1675.

Vivekanandhan, Singaravelu, et al.; "Biological Synthesis of Silver Nanoparticles using *Glycine max* (Soybean) Leaf Extract: An Investigation on different Soybean Varieties"; Journal of Nanoscience and Nanotechnology, vol. 9, No. 12; Aug. 14, 2009; pp. 6828-6833.

Kanchana, Amarnath, et al.; "Biogenic Silver Nanoparticles from *Spinacia oleracea*; and *Lactuca sativa* and their potential Antimicrobial Activity"; Digest Journal of Nanomaterials and Biostructures, vol. 6, No. 4; Nov. 10, 2011; pp. 1741-1750.

Ghiselli, Andrea, et al.; "A Fluorescence-Based Method for Measuring Total Plasma Antioxidant Capability"; Free Radical Biology & Medicine, vol. 18, No. 1; May 4, 1994; pp. 29-36.

Pellegrini, Nicoletta, et al.; "Total Antioxidant Capacity of Plant Foods, Beverages and Oils Consumed in Italy Assessed by Three Different in Vitro Assays"; The Journal of Nutrition, vol. 133; Jun. 20, 2003; pp. 2812-2819.

Haiss, Wolfgang, et al.; "Determination of Size and Concentration of Gold Nanoparticles from UV—Vis Spectra"; Analytical Chemistry, vol. 79, No. 11; Apr. 26, 2007; pp. 4215-4221.

Sheoran, V., et al.; "Phytomining: A Review"; Minerals Engineering, vol. 22; May 6, 2009; pp. 1007-1019.

Haverkamp, R.G., et al.; "The Mechanism of Metal Nanoparticle Formation in Plants: Limits on Accumulation"; J Nanopart Res, vol. 11; Oct. 24, 2008; pp. 1453-1463.

Hoagland, D.R., et al.; "The Water-Culture Method for Growing Plants without Soil"; University of California, College of Agriculture, Agricultural Experiment Station, Berkeley, California, Circular 347; Dec. 1938; 39 pages.

Murashige, Toshio, et al.; "A Revised Medium for Rapid Growth and Bio Assays with Tobacco Tissue Cultures"; Physiologia Plantarum, vol. 15; Apr. 1, 1962; pp. 473-497.

(56) References Cited

OTHER PUBLICATIONS

Sharma, Nilesh C., et al.; "Synthesis of Plant-Mediated Gold Nanoparticles and Catalytic Role of Biomatrix-Embedded Nanomaterials"; Environ Sci Technol., vol. 41, No. 14; Jul. 15, 2007; pp. 5137-5142.

De La Rosa, Guadalupe, et al.; "X-Ray Absorption Spectroscopy unveils the Formation of Gold Nanoparticles in Corn"; Acta Universitaria, vol. 19, No. 2; Sep. 2009; pp. 76-81.

Sharma, Nilesh C., et al.; "Chemical Speciation and Cellular Deposition of Lead in *Sesbania drummondii*"; Environmental Toxicology and Chemistry, vol. 23, No. 9; Feb. 20, 2004; pp. 2068-2073.

Krämer, Ute, et al.; "Subcellular Localization and Speciation of Nickel in Hyperaccumulator and Non-Accumulator *Thlaspi* Species"; Plant Physiology, vol. 122; Apr. 2000; pp. 1343-1353.

Salt, David E., et al.; "Zinc Ligands in the Metal Hyperaccumulator *Thlaspi caerulescens* as determined using X-Ray Absorption Spectroscopy"; Environmental Science & Technology, vol. 33, No. 5; Jan. 21, 1999; pp. 713-717.

Pickering, Ingrid J., et al.; "X-Ray Absorption Spectroscopy of Cadmium Phytochelatin and Model Systems"; Biochimica et Biophysica Acta, vol. 1429; Oct. 14, 1998; pp. 351-364.

Shen, Yuhua, et al.; "A Novel Biological Strategy for Morphology Control of $PbWO_4$ Crystals in Tomato Extract"; Colloids and Surfaces B: Biointerfaces 83; Dec. 2, 2010; pp. 284-290.

Voinnet, Olivier, et al.; "An enhanced transient Expression System in Plants based on Suppression of Gene Silencing by the p19 Protein of Tomato Bushy Stunt Virus"; The Plant Journal, vol. 33; Dec. 20, 2002; pp. 949-956.

Matic, Slavica, et al.; "Comparative Analysis of Recombinant Human Papillomavirus 8 L1 Production in Plants by a Variety of Expression Systems and Purification Methods"; Plant Biotechnology Journal, vol. 10; Nov. 17, 2011; pp. 410-421.

Xu, Ping, et al.; "Virus Infection improves Drought Tolerance"; New Phytologist, vol. 180; Aug. 10, 2008; pp. 911-921.

Jain, D., et al.; "Synthesis of Plant-Mediated Silver Nanoparticles using Papaya Fruit Extract and Evaluation of their Antimicrobial Activities"; Digest Journal of Nanomaterials and Biostructures, vol. 4, No. 3; Sep. 2009; pp. 557-563.

Benzie, Iris F.F., et al.; "Ferric Reducing/Antioxidant Power Assay: Direct Measure of Total Antioxidant Activity of Biological Fluids and Modified Version for Simultaneous Measurement of Total Antioxidant Power and Ascorbic Acid Concentration"; Methods Enzymol, vol. 299; Feb. 1999; pp. 15-27.

Song, Jae Yong, et al.; "Biological Synthesis of Gold Nanoparticles using *Magnolia kobus* and *Dopyros kaki* Leaf Extracts"; Process Biochemistry, vol. 44; Jun. 10, 2009; pp. 1133-1138.

\* cited by examiner

NANOPARTICLE SYNTHESIS USING PLANT EXTRACTS AND VIRUS

FIELD OF THE INVENTION

The present invention relates to nanoparticles, in particular metallic nanoparticles or metallised nanoparticles composed of metal and a virus or virus-like scaffold, and to a process for producing such particles.

BACKGROUND ON THE INVENTION

Nanoparticles are classified as fine particles sized between 1 and 100 nm. Significant research into the functions and uses of nanoparticles has been conducted since nanoparticles have been found to have utility in a broad range of fields, such as biomedicine, materials science, electronics, consumer products, pharmaceuticals, cosmetics, transportation and energy (see Hoeppner and Novobry 2012. Quarterly reviews of Biophys 45:209-255; and Wong 2012 Microchimia Action 117:245-270). Whilst nanoparticles formed from carbon material or dendrimers are known, much interest is also focused on metal nanoparticles or metallised nanoparticles. These are of particular interest for many applications in optoelectronics, electronics, biochemistry (including plant biochemistry) and medicine.

However, the production of metallic and metallised nanoparticles poses a number of problems. Metallic nanoparticles are commonly synthesized using hazardous chemicals such as sodium borohydride, tetrakishydroxymethylphosphonium chloride (THPC), poly-N-vinyl pyrrolidone (PVP), and hydroxylamine (Narayanan and Sakthivel, 2011 Adv. Colloid Interface Sci. 169:59-79). Other methods of nanoparticle production use aerosol deposition, laser ablation and lithography; which are not considered environmentally friendly. Moreover, the synthesis of metallic nanoparticles is expensive and time-consuming (Narayanan and Sakthivel, 2011, supra). Therefore, there is a clear need for simple, cost-effective and eco-friendly methods for the production of metallic nanoparticles (Raveendran et al., 2003 J. Am. Chem. Soc. 125:13940; Sharma et al., 2009 J. Colloid Interface Sci. 145:83; Narayanan et al., 2011 J. Colloid Interface Sci. 156:1). In recent years, it has been shown that biological systems including plants, algae (Govindaraju et al., 2008 J. Mater. Sci. 43:5115), diatoms (Scarano et al., 2002 Biometals 15:145; Scarano et al., 2003 Plant Sci 165:803), bacteria (Lengke et al., 2007 Langmuir 23:2694-2699) and human cells (Anshup et al., 2005 Langmuir 21:11562) can convert inorganic metal ions to metal nanoparticles. This typically uses a reductive process facilitated by proteins and metabolites contained in these organisms. Plant-based nanoparticle production has significant advantages over other biological systems. For example, plants are low maintenance, do not require sterile growth conditions and rapidly produce biomass. This is in contrast to the high cost and maintenance required to culture mammalian and bacterial cells. The low cost of cultivation, short time frame for production, safety and ability to scale up or down depending on demands make plants a particularly attractive nanoparticle synthesis platform.

Plant sap extracts can readily be used to reduce metal ions into metallic nanoparticles. This approach involves less downstream processing in order to extract the synthesized particles than other biological systems. The feasibility of this process has been demonstrated extensively using sap from a plethora of different plant species and a variety of metal acids and salts (including copper, gold, silver and iron). For example, *Pelargonium graveolens* extracts reduced gold ions into 20-40 nm decahedral and icosahedral shaped nanoparticles and stabilized them (Shankar et al., 2003, J. Mater Chem 13:1822), whereas *Cymbopogon flexuosus* extracts produced gold spheres and nanotriangles, ranging in size from 0.05-18 μm (Shankar et al., 2004 Nat Mater 3:482). *Azadirachta indica* extract has been used to reduce chloroauric acid ($HAuCl_4$) into gold planar triangles and hexagons ranging in size from 50-100 nm (Shankar et al., 2004 J. Colloid Interface Sci 275:496). This study also reported that *A. indica* sap can reduce silver nitrate into polydispersed spherical nanoparticles of 5-25 nm in size (Shankar et al., 2004 J. Colloid Interface Sci 275:496). In addition, *Aloe barbadensis* leaf extract has been used to produce cubic 5-50 nm $In_2O_3$ particles (Maensiri et al., 2008 J Optoelectron Adv Mater 10:161). The nanoparticles formed are predominately metal in content.

However, it should also be noted that in addition to dispersed nanoparticles these techniques often produce massive micron-sized metallised and/or metallic aggregations significantly lowering the yield of "real" nanoparticles (see FIGS. 1*a*, 2 and 3). In the context of the present invention, as understood by those in the present field, a "real" nanoparticle, as discussed herein, is considered to be a metallised and/or metallic nanoparticle that has at least one dimension less than 100 nm. Moreover, these processes do not always allow preparation of uniform (in size and architecture) nanoparticles with a specific morphology, which is highly important for many technological applications.

In a separate approach, viruses or virus-like particles were shown to serve as biotemplates for metal deposition, forming metallised nanoparticles in a specific manner (Kadri et al., 2011 Virus Research 157:35-46; Aljabali et al., 2010 Nanoscale 2:2596-2600). For example, the external or internal surfaces of cowpea mosaic virus (CPMV), brome mosaic virus (BMV), potato virus X (PVX) and tobacco mosaic virus (TMV) particles have been coated with different metals. Since TMV particles expose several distinct surfaces suitable for metallization (Balci et al., 2012 Nanotechnology 23; Knez et al., 2006 Nano Lett. 6: 1172-1177) or functionalization with organic molecules (Endo et al., 2006 Chemistry 12:3735-3740; Shimizu et al., 2005 Chem Rev 105: 1401-1443), they have been exploited as promising biotemplates for nanoscale materials (Lee et al., 2012 Biotechnol. Bioeng. 109:16-30). Due to their physical and chemical stability they are attractive tools for inorganic nanostructures (Bitner et al., 2005 Naturwissenschaften 92:51-64, Dujardin et al., 2003 Nano Lett. 3:413-417). Dujardin et al. (2003, supra) and Knez et al. (2006, supra) used the plant-derived virions to produce nanowires by selective metallization of the outer surface or the inner channel. For fabrication of thin film-embedded nanostructures, TMV was utilized as a nanobiotemplate in atomic layer deposition systems producing metal oxide nanotubes (Knez et al., 2006, supra). Most importantly, functional electronic devices (Atanasova et al., 2011 Adv. Mater. 23:4918-4922; Chen et al., 2011 Electrochim. Acta 56:5210-5213) as well as ferrofluids (Wu et al., 2010 ACS Nano 4:4531-8) were designed on the basis of TMV biotemplates.

SUMMARY OF INVENTION

The inventors have investigated the use of virus as additives in nanoparticle synthesis reactions within plants or plant extracts. In particular the inventors have investigated TMV (300 nm rods of 18 nm diameter) and Bovine papillomavirus-like particles (BPV VLPs; 30 nm diameter non-infectious spherical particles composed of the coat protein only) as additives in nanoparticle synthesis reactions composed of *Nicotiana benthamiana* sap extracts and metal salts/acids. The electron microscopy results from these experiments were unexpected. Addition of virus/virus-like particles to the reaction mix not only led to metallization of virus particles but also greatly enhanced the yield and monodispersity of metallic nanoparticles and additionally influenced the architecture of the dispersed nanoparticles formed.

Accordingly, in a first aspect, the present application provides a process for production of metal-coated virus particles, said process comprising admixing virus particles with plant material, suitably a plant extract, in particular a plant sap extract with reducing power and a metal salt.

In a second aspect, the present invention provides a process for production of metallic nanoparticles, said process comprising admixing virus particles with plant material, suitably a plant extract, in particular a plant sap extract with reducing power and a metal salt. The metallic nanoparticles will be substantially formed of metal, but may include other components, for example components from the plant sap conjugated to the metal. Usually the metallic nanoparticle will comprise at least 80% by weight of metal (for example at least 90% or at least 95% by weight of metal) relative to the total weight of the nanoparticle.

Without wishing to be bound by theory, in the process it is considered the metal salt is a precursor in the reaction and the salt gets reduced to form metal atoms of lower valency. These atoms can act as seeds for subsequent nucleation events which lead to nanoparticle formation.

As noted above, the method of the present invention has the surprising benefit that the metallic nanoparticles and/or metal-coated virus particles exhibit reduced aggregation, thereby increasing the useful yield of metal-coated nanoparticles. A further benefit is the additional or alternative formations of nanoparticles produced. In embodiments use of virus particles in the process can increase the yield of nanoparticles by at least 2 fold, at least 3 fold, at least 4 fold, at least 5 fold over a process which does not utilise virus particles. In embodiments, use of virus particles in the process can increase the monodispersity of the nanoparticles by at least 2 fold, at least 3 fold, at least 4 fold, at least 5 fold over a process which does not utilise virus particles.

In the context of the present invention, a nanoparticle, as discussed herein, is considered to be a metallised and/or metallic and have at least one dimension less than 100 nm. For example a TMV metallised and/or metallic nanoparticle may have a diameter or about 18 nm, but a length of about 200 nm. In embodiments, the nanoparticle can be less than 100 nm in every dimension.

The term "virus particle" as used herein references any non-enveloped virus particle (VP) whether or not infectious, including virus-like particles (VLP) which lack nucleic acid content. Examples of suitable virus particles include non-enveloped viruses having a capsid coat, for example a helical capsid, a filamentous capsid or an icosahedral capsid. Particular examples of helical (rod-shaped) viruses include tobacco mosaic virus (TMV), tobacco rattle virus (TRV), barley stripe mosaic virus (BSMV) and peanut clump virus (IPCV). Particular examples of filamentous viruses are citrus tristeza virus (CTV), ebola virus and potato Virus X (PVX). Particular examples of icosahedral viruses include bovine papillomavirus (BPV), potato leaf roll virus (PLRV), cowpea mosaic virus (CPMV), polio virus, cauliflower mosaic virus (CaMV) and bluetongue virus, and the like.

In addition to the plant and animal viruses indicated above, bacteriophages may have utility in this process. In embodiments the bacteriophages can contain linear dsDNA (Rudiviridae and Podoviridae), circular dsDNA (Bicaudaviridae and Corticoviridae), circular single stranded DNA (Microviridae), linear ssRNA (Leviviridae) or dsRNA (Fuselloviridae). In embodiments, bacteriophages of utility for this invention can have isometric (Corticoviridae), lemon-shaped (Fuselloviridae), ovoid (Guttavirus), bottle-shaped (Ampullaviridae), rod-shaped (Rudiviridae), filamentous (Inoviridae) and pleomorphic (Plasmaviridae) morphologies. In embodiments, bacteriophages of utility may have (Myoviridae) or may not have contractile tails (Siphoviridae).

Use of rod-shaped, filamentous and spherical viruses can lead to correspondingly shaped nanoparticles and can significantly improve nanoparticle synthesis and yield. In embodiments the virus can include nucleic acid (RNA; TMV, PVY). In embodiments the virus can lack viral nucleic acid (empty Cowpea mosaic virus, eCPMV; and Bovine papillomavirus-like particles, BPV VLPs). In embodiments, virus lacking nucleic acid can be prepared or obtained according to Love et al., 2012 (BPV VLPs) and Saunders et al., 2009 (eCPMV).

In embodiments, transgenic and/or chemically modified viruses (for example TMV and eCPVM), with altered surface display metal binding and reducing peptides, can be utilised for production of nanoparticles in the present invention. In embodiments, genetically or chemically modified viruses that surface display peptides or motifs which have metal ion binding and/or reducing properties, to provide surface functionalized viruses (displaying peptides that can bind and aid reduction of metal ions into nanoparticles) can be provided in a plant or admixed with plant material, such as plant sap. In embodiments, gold, silver and iron nanoparticles can be produced using different metal salts using genetically modified viruses.

Inclusion of at least one non-enveloped virus particle (such as rod-shaped (such as TRV or BSMV), filamentous (for example, CTV or PVX) or icosahedral (such as BPV, PLRV, CaMV or CPMV) viruses or their VLP derivatives in the plant reaction mix with metal salts/metal acids such as $HAuCl_4$, $KAuCl_4$, $AgNO_3$, $In(OCCH_3CHOCCH_3)_3$, $PdCl_2$, $H_2PtCl_6 \cdot (H_2)_6$ and $Ag(NH_3)_2NO_3$ leads to the production of monodisperse metallic nanoparticles and also a diverse array of metallised viral particles. Inclusion of said viral structures in the reaction mix can also modulate the morphologies of the metallic nanoparticles produced.

The plant extract can be obtained from any suitable plant material, such as leaves, stalks or the like. It will be understood from the teaching of methods of extraction of plant sap, that sap can be considered to be a plant extract. A plant sap extract can be used, i.e. the plant sap can be extracted from the plant, so that the process is conducted ex planta. Optionally, the plant sap extract is treated and/or purified prior to use. As will be understood from the art, the plant sap comprises a reducing agent. The amount of plant sap used in the processes disclosed herein is sufficient to convert substantially all of the admixed dissolved metal ion into nanoparticles. As used herein, substantially all comprises greater than 50%, at least 60%, 70%, 80%, 85%, 90% or more.

It will be understood from the teaching of methods of extraction of plant sap, that sap can be considered to be a plant extract. Plant extract can be obtained from plant parts and components at different levels of processing. The plant extract may not exclusively or directly contain sap isolated from plant vascular networks (xylem/phloem). In embodiments plant extract can relate to any aqueous or non-aqueous components taken from any part of a plant; for example waste dried potato peelings or fresh fruits when used in conjunction with virus and metal salts for nanoparticle production could constitute a further embodiment of the invention. In embodiments the plant extract can be a plant sap extract, wherein the sap is considered to be limited to components transported in xylem and phloem.

Metal salts suitable for use in any process according to the invention include salts of metals excluding the alkali metals and alkali earth metals of Groups IA and IIA. Suitable metals include transition metals and Al, Ga, In, Ge and Sn. Particular examples include silver, gold, iron, copper, indium, platinum, palladium, rhodium, manganese, zinc, molybdenum, iridium, cobalt and the like. Optionally the metal salts can be salts of silver, gold, iron, indium, platinum, palladium, rhodium, cobalt or iridium. In embodiments, the metal salt can have a positive reduction potential greater than 0.2V, for example greater than 0.4V. For example, $HAuCl_4$, $KAuCl_4$, $AgNO_3$, $In(OCCH_3CHOCCH_3)_3$, $PdCl_2$, $H_2PtCl_6 \cdot (H_2O)_6$, $Ag(NH_3)_2NO_3$ are suitable, although the invention is not limited to these particular salt types.

In use, the metal salts are provided in the process as a metal ion, suitably a metal ion in solution, provided by dissolving a metal salt in solution. In embodiments the dissolved metal ion can be provided by dissolving a metal chelate in solution. In embodiments, a metal ion can be provided by a metal acid. Suitably, in embodiments of the invention, in the context of the present invention, a metal chelate or a metal acid can be considered as a metal salt.

The plant sap can be extracted by techniques known in the art from any suitable plant material, for example, leaf, stem, fruit etc. Exemplary protocols for extracting the plant sap are described in Yilmaz et al., (2011 Mater Chem and Phys 130:1195-1202) and Song et al., (2009 Bioprocess Biosyst Eng 32:79-84). For example, *Stevia rebaudiana* leaf material was air dried and finely crushed using a 200 µm mesh filter. Then 0.1 g of the leaf filtrate was added to 50 ml deionized water and then stirred for 1 hour at room temperature. The extract was filtered and centrifuged at 10,000 rpm in order to remove debris. The clear extract was then used to reduce metal salts into nanoparticles (Yilmaz et al., 2011, supra). As a further example, extracts from *Pinus desiflora, Diopyros kaki, Gingko biloba, Magnolia kobus* and *Platanus orientalis* could each be obtained by combining 5 g of finely cut leaf material with sterile distilled water before boiling for 5 minutes. Upon cooling the sap extracts can be used in nanoparticle synthesis reactions (Song et al., 2009, supra). Similarly, nanoparticles can also be produced using sap extracts from *Nicotiana benthamiana*; in this case fresh leaf material was ground in liquid nitrogen into a fine powder and then added to distilled deoionized water to a ratio of 2.5:1 (w/v) before boiling for 15 minutes. The extracts were passed through two layers of muslin, and the liquid was centrifuged for 5 minutes at 16,000 g. The supernatant was collected and appropriately diluted prior to use in the nanoparticle synthesis reactions.

An additional example is the preparation of aqueous extracts from *Carica papaya* fruits, whereby 25 g of *papaya* fruit were crushed into 100 ml of distilled water and sequentially filtered through Whatman No. 1 filter paper (pore size 25 µm) and then through 0.6 µm sized filters (Jain et al., 2009 Dig J Nanomat and Biostruct 4: 723-727). The extracts were subsequently used in nanoparticle synthesis reactions.

The present invention is not limited to any particular plant type as a source of plant sap or plant extract. Plant extract or plant sap may be obtained from a variety of dicotyledonous and monocotyledonous plants.

Suitable plants to provide plant material, in particular plant extract, suitably plant sap extract to provide to the process of the present invention or in which to provide the process when conducted in planta, include *Nicotiana* sp., *Musa* sp., *Psidium* sp., *Avena* sp., *Azadirachta* sp., *Chenopodium* sp., *Syzygium* sp., *Citrus* sp., *Glycine* sp., *Spinacia* sp., *Carica* sp., *Stevia* sp., *Pinus* sp., *Diopyros* sp., *Gingko* sp., *Magnolia* sp., *Platanus* sp. and the like. *Nicotiana benthamiana* is a suitable source of plant sap. Other suitable examples include *Musa pradisiaca* (Bankar et al., 2010 Colloids Surf B 80:45-50), *Psidium guava* (Raghunandan et al., 2009 Nano Biotechnol 5:34-41), *Avena sativa* (Armendariz et al., 2004 J. Nanopart Res 6:377-382), *Azadirachta indica* (Shankar et al., 2004, supra), *Chenopodium album* (Dwivedi and Gopal, 2010 Colloids Surf A 369:27-33), *Syzygium aromaticum* Singh et al., 2010 J. Nanopart Res 12:1667-1675), *Citrus* (including *Citrus aurantifolia*), *Glycine max* (Vivekanandhan et al., 2009 J. Nanosci Nanotechnol 9:6828-6833), *Spinacia oleracea* (Kanchana et al., 2011 Digest J Nanomat and Biostruct 6:1741-1750), as well as the sources noted above.

In embodiments, crop plants (or waste material from crop plants i.e. straw from wheat or barley, potato peelings, waste fruit pulp etc) can be used in this process: For example, *Hordeum vulgare* (barley), *Triticum* spp (wheat species), *Zea mays* (corn), *Oryza sativa* (rice), *Solanum tuberosum* (potato), *Daucus carota* (carrot), *Brassica* spp (turnip, swede, cauliflower etc), *Beta vulgaris* (sugar beet), *Saccharum* (sugar cane), *Solanum lycopersicum* (tomato) and *Vitis* (grape) or an extract thereof may be used in the process.

A plant sap extract for use in the process of the present invention can be characterised by its capacity to reduce metal ions into nanoparticles.

The assays outlined below can be used to give a relative and qualitative guide as to what plant types or plant parts contain the highest reducing power or capacity, and thus may be advantageously used to reduce metal salts into nanoparticles.

Such reductive power or capacity can be predicted by the use of suitable tests such as the ferric reducing-antioxidant power test (FRAP; Benzie and Strain, 1999 Methods Enzymol. 299:15-27) or the total radical-trapping antioxidant parameter (TRAP; Ghissello et al., 1995 Free Radic. Biol. Med. 18: 29-36). Such methods have been used previously to document the reducing power of a variety of plants, parts of plants and plant products (Pellegrini et al., 2003 J. Nutr. 133: 2812-2819). This can allow identification of those candidate extracts or sap extracts able to reduce nanoparticles. A further example of determining the suitability of plant extracts or sap extracts for production of nanoparticles is to measure their production in the reaction mix using UV-visible absorbance assays. In a suitable assay, boiled (eg. *N. benthamiana*) leaf extracts and chloroauric acid are combined (extracts were 100-fold diluted in the reaction mix and chloroauric acid was added to $2.9 \times 10^{-4}$M final volume) and the reaction progression assessed by measuring absorbance spectra from 300-700 nm in a spectrophotometer. Over time the absorbance of the reaction increases beyond that observed for the individual separate reaction components. A peak clearly discernible at around 550 nm, correlates to the formation of ~60 nm gold nanoparticles. A peak having wide shoulders stretching from 500 nm-580 nm indicates production of a variety of sizes and shapes of gold nanoparticles. A similar approach can be undertaken with *Syzygium aromaticum* extract, which can be combined in a 1:1 ratio with $4\times10^{-3}$M chloroauric acid and then 20-fold dilutions made of the reaction mix before analyzing the UV-visible spectra on a spectrophotometer. A peak in absorbance observed at 515 nm, the magnitude of which increases until conclusion of the reaction (Singh et al., 2010 supra), indicates nanoparticle formation. The absorbance peaks for gold nanoparticles vary depending on particle size and shape; for example simple 10-100 nm spherical particles have peaks in the 500 nm-600 nm range. This not only constitutes a useful tool for confirming that a plant sap extract can directly produce nanoparticles, but can allow a preview of what particle sizes may be present (Haiss et al., 2007 Anal. Chem. 79:4215-4221).

Generally at least 5 µl undiluted plant (optionally diluted up to 20 fold in water) can be used in the admixture. For example from 5 µl to 50 µl plant extract or sap can be used, for example 10 µl to 30 µl, for example 15 µl to 25 µl. In some situations it may be more convenient to use the plant extract or sap in diluted form. Where the plant extract or sap has been diluted, the volume of the diluted plant extract or sap added can be increased accordingly. For example, instead of 20 µl plant extract or sap, 200 µl of a 10× dilution can be used.

In embodiments the process of the invention can be carried out at a temperature in the range 0° C. to 60° C., suitably from 4° C., 10° C., 15° C., 20° C., 25° C., 30° C., 35° C., 40° C., 45° C., 50° C. to 100° C.

In embodiments, the temperature at which the process can be conducted is in the range 5° C. to 25° C., advantageously 10° C. to 20° C.

In embodiments, changing the temperature can affect metal nanoparticle morphology. For example Lukman et al., (2011) found that increasing the reaction temperature higher than 30° C. led to the formation of silver nanotriangles from silver salts. In another example, in which *Cassia fistula* extracts were used, silver nanowires were obtained at room temperature, whereas at 60° C. spherical nanoparticles and short rods were observed (Lin et al., 2010). Using *Nyctanthes arbortristis* extracts in conjunction with gold salts, gold triangles, pentagons, rods and spheres were obtained at 25° C., whereas predominantly spherical nanoparticles were obtained at 80° C. (Das et al., 2011

In embodiments the process of the invention can be carried out at atmospheric pressure.

In embodiments the process can be performed at a pH in the range pH 4 to pH 8.

In embodiments the nanoparticles provided by any process of the invention can comprise two or more metals. In embodiments a first metal salt can be admixed to the plant extract and virus particle at a first time point and a second or subsequent metal salt can be admixed at a second time point after a period of time. Alternatively the first and second metal salt can be admixed with the plant extract and virus particle simultaneously.

As will be understood, based on the reducing power of the plant material or extract, metal nanoparticles are synthesised by reducing the corresponding metal salt solutions. In embodiments, the metal nanoparticle can be an iron nanoparticle, a manganese nanoparticle, a gold nanoparticle, a platinum nanoparticle, a copper nanoparticle, an indium nanoparticle, a silver nanoparticle, an indium nanoparticle, an iridium nanoparticle, a rhodium nanoparticle, a palladium nanoparticle, a cobalt nanoparticle or combinations thereof.

In embodiments the metal nanoparticles can have zero valency. However plant synthesized nanoparticles can have different and possibly modulatable surface charges that are dependent on what biomolecular components of the extract are associated with the nanoparticle.

Suitable concentrations of metal salts or metal ions in solution for use in any process of the invention include concentrations from 1M to $1\times10^{-5}$M, in particular concentrations between $2.5\times10^{-3}$M to $2.9\times10^{-4}$ M.

Metal salts more recalcitrant to reduction into nanoparticles would typically be used at higher concentrations (0.5M $Co(NO_3)_2$) and in conjunction with either more concentrated plant extracts (such as neat *Hordeum vulgare* extracts) or extracts with more potent reducing ability (such as ten-fold dilutions of *Rubus fruticosus* extracts), or a combination of both to produce nanoparticles. Where metal nanoparticles can be formed at certain metal salt to plant extract ratios, it is important to note that refinement to this ratio can influence nanoparticle number and size. In embodiments varying the ratio can influence metal nanoparticle shape, either by the increased presence of nanoparticle shape modifying biomolecules, or of more stabilizing agents which may enhance the stability of nanoparticles with unstable morphologies.

Virus particles and virus-like particles (VLPs) used in the process can be used at concentrations ranging from 400 µg to 30 ng per 200 µl nanoparticle synthesis reaction volume. For example, a reaction mixture can consist of: 170 µl sap extract, 20 µl of 10× concentrated metal salt and 10 µl of virus or VLPs.

This range of virus concentration has typically been most efficient in the ex planta reaction. Due to the variation in the surface chemistries of the viruses which likely influence the different degrees of metal binding and reduction, the most efficient virus concentration has to be empirically determined for a given metal salt and plant extract. Typically, this is achieved by admixing a range of concentrations or virus solution with the metal salt and plant extraction.

Alternatively, the process of the present invention can be conducted in planta. Thus, in one aspect the process of the present invention for production of metallic or metallised nanoparticles comprises:
  i) providing a plant infected with a non-enveloped virus and/or able to express a non-enveloped virus particle; and
  ii) exposing said plant to a concentration of a water-soluble metal salt sufficient for nanoparticle formation.

In an alternative aspect, the process of the present invention for production of metallic or metallised nanoparticles comprises:
  i) providing a plant and exposing said plant to a concentration of a water-soluble metal salt sufficient for nanoparticle formation; and
  ii) exposing said plant to a non-enveloped virus and/or a genetic construct able to express a non-enveloped virus particle.

In in planta embodiment, optionally the metal salt can be selected from a metal other than potassium, iron, calcium, manganese, zinc, molybdenum, copper or cobalt. Optionally the concentration of water-soluble metal salt sufficient for nanoparticle formation can be provided above the concentration used for a microelement in a hydroponic solution and/or is above the levels of such elements in soil or planting compost, for example is 100 ppm or more for copper, or 100 ppm or more for iron.

In embodiments, the non-enveloped virus causes the plant to produce virus particles due to infection of plant tissue.

Usually the non-enveloped virus is an infectious (ie. self-replicating) virus. The infection can be a localised infection or can be systemic. Alternatively tissues of the plant can be modified genetically by nucleic acid material expressing capsid proteins, which self-assemble to form virus-like particles. The genetic material encoding the capsid proteins can be DNA or RNA, and can be single or double-stranded. The genetic material can be part of an expression vector used to transfect the plant or the plant genome itself could be genetically modified so that the plant is transgenic.

Virus like particles that can be exploited in the process of the invention can include, for example, the coat proteins of Cowpea mosaic virus, Bovine papillomavirus, Human papillomavirus, core antigen of the hepatitis B virus (forms non-enveloped structures in plants) and Blue tongue virus when expressed in plants self-assemble to form virus like particles (Thuenemann et al., 2013).

Conveniently, the plant for use in a process of the invention can be grown hydroponically. Optionally the plant can be salt-tolerant, for example can be a plant which grows well in coastal or estuary conditions. Specific examples include *Thellungiella halophila, Atriplex nummularia* and *Rosa Rugosa*. Alternatively or additionally the plant can have the capacity to hyperaccumulate metal ions, for example *Brassica juncea, Thlaspi caerulescens, Ipomea alpine* and *Sinapis alba* (Sheoran et al., 2009 Miner Engin 22: 1007-1019).

As discussed herein in relation to the first aspect of the invention, a variety of dicotyledonous and monocotyledonous plants can be utilized for production in planta of nanoparticles composed of different metals. Further, as discussed herein in relation to the first aspect of the invention, a diverse set of viruses can be utilised for in planta production, and the virus utilised may improve nanoparticle synthesis and yield. In embodiments, the virus can contain nucleic acid or lack nucleic acid.

A plethora of different metal salts have been used in conjunction with plant extracts and whole plants grown hydroponically to produce metal nanoparticles (Gan and Li, 2012, Rev Environ Sci Biotechnol 11:169-206; Narayanan and Sakthivel, 2011 Adv. Colloid Interface Sci. 169:59-79). These prior art methodologies can be enhanced in terms of nanoparticle yield and/or nanoparticle type by exposing the plant tissue to a virus or virus-like particle in accordance with the present invention.

For in vitro synthesis of metallic nanoparticles from plant extracts and metal salts, concentrations of metal salts have varied from $1\times10^{-1}$M to $1\times10^{-4}$M (Gan and Li, 2012, supra; Narayanan and Sakthivel, 2011 Adv. Colloid Interface Sci. 169:59-79). For nanoparticle synthesis using whole plants, the metal salt of interest can be added to the plant (conveniently as part of a hydroponic solution) at a concentration range of 25 to 10,000 ppm, suitably greater than 50 ppm, 100 ppm, 200 ppm, 500 ppm, 1000 ppm, 2000 ppm, 5000 ppm. The concentration of the metal salt of interest added to a hydroponic solution for in planta nanoparticle generation is typically beyond that of the trace amounts of potentially reducible metal salts already present in the hydroponic solution. Commonly used hydroponic solutions contain trace metals to ensure appropriate plant nutrition and robust growth, for example, 1-5 ppm iron, 0.5 ppm manganese, 0.05 ppm zinc, 0.02 ppm copper and 0.01 ppm molybdenum are often found in such solutions (Haverkamp and Marshall, 2009, J Nanopart Res 11:1453-1463; Hoagland and Arnon, 1938 Agric. Exper. Sta., Berkeley Circ. 347. 39 pp.). An additional example of the trace metal salts in a hydroponic nutrient formulation is 0.0250 ppm $CoCl_2$, 0.0250 ppm $CuSO_4$, 27.8 ppm $FeSO_4$, 8.6 ppm $ZnSO_4$ (Murashige T and Skoog F, 1962 Physiol Plant 15: 473-497). Such formulations which are commonly used in hydroponic cultivation practices, do not lead to the formation of in planta metal nanoparticles; in consequence the present invention can use conventional hydroponic solutions as a medium supplemented with higher concentrations of meta f salts of interest that generate the desired metal nanoparticles in planta. For example, inclusion of silver nitrate (or other silver salts such as $Na_3Ag(S_2O_3)_2$, and $Ag(NH_3)_2NO_3$) in the hydroponic solution in the ranges of 2,500 to 10,000 ppm led to the accumulation of 2-35 nm silver nanoparticles in *Brassica juncea*; the highest nanoparticle concentration obtained was approximately 0.35% of plant dry weight (Haverkamp and Marshall, 2009, supra). Another example is the addition of potassium tetrachloroaurate to the hydroponic media of *Sesbania drummondii* plants at a concentration of 200 ppm. In this case reduced gold was detected from 9 g/kg dry weight in the roots to 100 mg/kg dry weight in the shoots (Sharma et al., 2007 Environ Sci Technol 15:5137-5142). 200 ppm was found to give the optimal yield of nanoparticles, whereas as 25 ppm produced very few nanoparticles. Moreover, it has also been shown that *Zea mays* grown in media supplemented with potassium tetrachloroaurate at 20 ppm to 160 ppm was able to uptake and reduce the gold ions into nanoparticles (Rosa et al., 2009 Acta Univers. 19:76-81). Determination of a suitable concentration of metal salt for any given plant species can thus be made in accordance with known methodologies. Metal salts have different reduction potentials, such that some may be more amenable to nanoparticle formation than others. Previous reports have shown that plants can produce nanoparticles from Au, Ag and Cu salts that have positive reduction potentials (V) (Gan and Li, 2012, supra). Moreover, metals (in complex with chloride, for example) such as Ru (0.46 V), Rh (0.5 V), Pd (0.64 V), Ir (0.86 V) and Pt (0.74 V) are also likely to be reduced into nanoparticles due to their positive reduction potentials (Haverkamp and Marshall 2009, supra). In contrast, the plant-mediated formation of nanoparticles is much less efficient for metals that have negative reduction potentials, for example: $Pb^{2+}$ to $Pb^0$ at −0.13 V (Sharma et al., 2004 Environ Toxicol Chem. 23: 2068-2073), $Ni^{2+}$ to $Ni^0$ at −0.24 V (Kramer et al., 2000 Plant Physiol 122:1343-1353), $Zn^{2+}$ to $Zn^0$ at −0.24 V (Salt et al., 1999 Environ Sci Technol 33:713-717), $Co^{2+}$ to $Co^0$ at −0.28 V, $Fe^{2+}$ to $Fe^0$-0.44 V, $Cd^{2+}$ to $Cd^0$ at −0.40 V (Pickering et al., 1999 BBA-Protein Struct Mol Enzymol 1429:351-364). In addition, although some metals may not be fully reduced in the plant system, they may be reduced to such an extent that facilitates their interaction with other partially reduced metals, such as has been observed with using tomato extract to produce lead tungstate crystals from $PbO_2$ and $Na_2WO_4.2H_2O$ (Shen et al. 2011 Colloids Surf B Biointerfaces 2011:83-284).

Suitably metals that have a reduction potential can be used in the process of the invention from 1.5 V (gold (III)) to −0.44 V (iron(II)),). The reduction power or capacity of a plant can vary according to the level of antioxidant biomolecules present. This may change according to the growing and harvesting conditions and also the plant species (Gan and Li, 2012).

In one embodiment, the invention provides a method for forming metallised nanoparticles, said method comprising: admixing at least 100 μg non-enveloped virus particles with a 1M to $1\times10^{-5}$M, suitably metal salt in the presence of at least 5 μl plant sap (for example from any of the plants discussed above).

It is considered that 100 μg of virus could amount to around $1.51\times10^{12}$ virus particles (Tobacco mosaic virus), or $1.53\times10^{13}$ eCPMV particles for example.

As will be understood, the final concentrations of the plant material or extracts and metal salts in the reaction mix determine the progression of nanoparticle formation. These concentrations can be obtained using a variety of approaches; for example either through addition of larger volumes of more dilute plant extracts or smaller volumes of more concentrated plant material or extracts. Plant extracts containing high levels of antioxidants have great metal salt reducing power (i.e *Rubus fruticosus* and *Hordeum vulgare*) and can be used at lower concentrations for nanoparticle production than plant material or extracts with weaker metal salt reducing power (*N. benthamiana* for example).

A metal salt for use in any process of the present invention can be a salt of iron, copper, gold, silver, indium, platinum, palladium, rhodium, iridium or a mixture thereof. For example, the metal salt can be $HAuCl_4$, $AgNO_3$, $In_2O_3$ or a mixture thereof.

In embodiments, the virus particles can be TMV, TRV, BSMV, IPCV, CTV, PVX, BPV, PLRV, CPMV, CaMV, polio, bluetongue or ebola virus or mixtures thereof. Non-infectious forms of each of these particles can also be used.

The metallic and metallised particles formed in the process of the present invention as described above may be unique in comparison to other metallic and metallised virus particles due to the incorporation of plant-derived biomolecules, and the distinct reaction kinetics of the process. Accordingly the present invention also encompasses the metallised nanoparticles produced as described above. These metallised nanoparticles can have numerous uses, including electronics, biomedicine, pharmaceuticals, cosmetics, biochemistry and plant biochemistry.

In embodiments, the metallic nanoparticles of the invention can be sized between 5 nm to 100 nm. In embodiments, the nanoparticles can have a diameter from about 10 nm to 100 nm, suitably from about 20 nm to 85 nm, or 10 nm to 50 nm or greater than 15 nm, greater than 25 nm, greater than 30 nm, greater than 40 nm, greater than 50 nm, greater than 60 nm, greater than 70 nm, or greater than 80 nm.

In embodiments the majority of nanotechnological applications will utilize metal nanoparticles in the 5-100 nm size range. Smaller nanoparticles such as 5-40 nm have larger surface to volume ratios than bigger nanoparticles and as such they may be of more use in catalysis or drug delivery. Moreover, particles of such sizes can have unusual optical characteristics (strong surface plasmon resonance) which may be more likely to be exploited in biosensor applications (for example) than larger nanoparticles. In general smaller nanoparticles are more reactive by virtue of their large surface to volume ratio, and consequently may be less stable; larger particles maybe more suited when greater structural integrity of nanoscle devices is required for example.

According to a further aspect of the present invention, there is provided a structure formed by nanoparticles provided by any process of the invention.

In embodiments, a nanoparticle structure can have various shapes including spheres, rods, prisms, hexagonal and mixed prisms and other shapes.

In embodiments, advantageously spherical nanoparticles are provided.

In yet another aspect, the invention provides devices comprising a metal nanoparticle prepared according to any of the methods disclosed herein. Suitably, the device may be, for example, a medical diagnostic test, a targeted delivery device or electronic device.

Each document, reference, patent application or patent cited in this text is expressly incorporated herein in their entirety by reference, which means it should be read and considered by the reader as part of this text. That the document, reference, patent application or patent cited in the text is not repeated in this text is merely for reasons of conciseness.

Reference to cited material or information contained in the text should not be understood as a concession that the material or information was part of the common general knowledge or was known in any country.

Throughout the specification, unless the context demands otherwise, the terms 'comprise' or 'include', or variations such as 'comprises' or 'comprising', 'includes' or 'including' will be understood to imply the includes of a stated integer or group of integers, but not the exclusion of any other integer or group of integers.

Preferred or alternative features of each aspect or embodiment of the invention apply mutatis mutandis to each other aspect or embodiment of the invention, unless context demands otherwise.

BRIEF DESCRIPTION OF THE FIGURES

The present invention will now be further described by reference to the following, non-limiting examples, and figures in which.

EXAMPLES

Example 1

Figure 1:
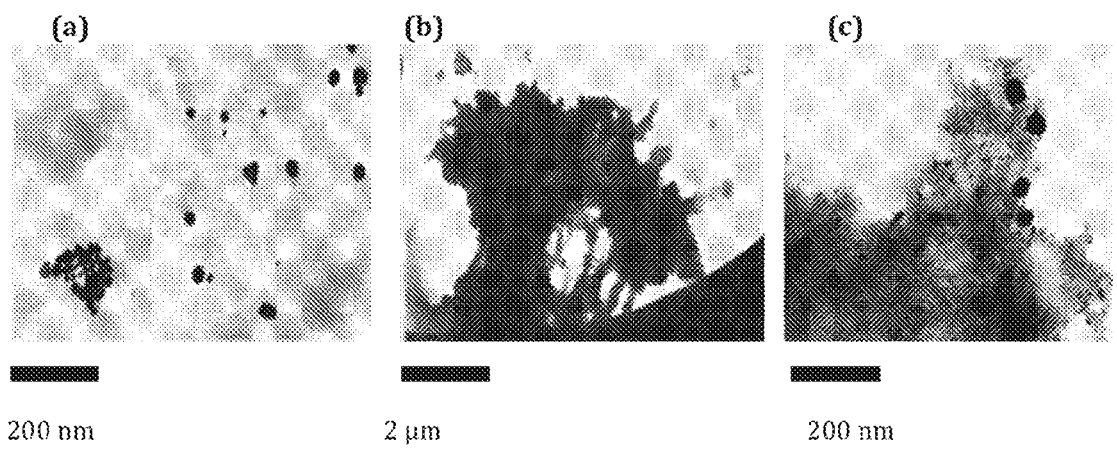
FIG. 1. EM analysis of the gold (a, b) and silver (c) structures formed after addition of a 10-fold dilution of *N. benthamiana* sap to chloroauric acid ($2.9 \times 10^{-4}$M) or silver nitrate ($2.5 \times 10^{-4}$M) in the absence of virus/virus-like particles. (a) Small numbers of 10-30 nm gold nanotriangles, spheres and hexagons; (b) aggregated metallized gold material; (c) aggregated conglomerates of silver nanoparticles of diverse sizes and morphologies formed after addition of a 10-fold dilution of *N. benthamiana* sap to silver nitrate ($2.5 \times 10^{-4}$M).
Figure 2:
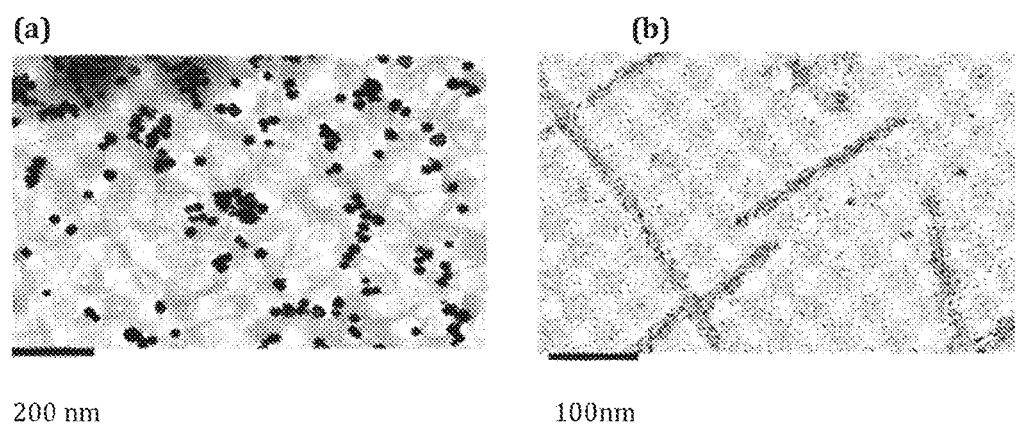
FIG. 2. EM analysis of the gold nanoparticles formed after addition of a 10-fold dilution of *N. benthamiana* sap to chloroauric acid ($2.9 \times 10^{-4}$M) in the presence of TMV particles. (a) TMV networks decorated with disperse 15-40 nm gold nanoparticles observed after the addition of 0.32 μg/200 μl TMV to the reaction mix. (b) Metallization of TMV observed after addition of high concentrations of TMV (320 μg/200 μl) to the reaction mix.

TMV Enhances the Yield and Uniformity of Gold Nanoparticles in the Biosynthesis Reactions Initial experiments with chloroauric acid and filtered *N. benthamiana* sap extracts, led to rapid reduction of the gold ions into gold aggregates which were thought to be imbedded in amorphous biological material; dilution of sap and chloroauric acid prevented aggregation to some extent but compromised the number of discrete nanoparticles formed. For example, it was found that using HAuC14 at $2.9 \times 10^{-4}$ M, with 10-fold dilutions of the sap extract produced discrete gold nanotriangles and hexagons ranging from 10-100 nm in diameter (FIG. 1a). However, it was also observed that in addition to dispersed nanoparticles, massive micron-sized metallized amorphous aggregations were still commonly observed (FIG. 1b). These aggregates likely lowered nanoparticle numbers (yield) by sequestering available metal ions. Addition of TMV to the 10-fold diluted sap reaction mix (0.32 µg/200 µl) led to formation of reticulate TMV matrices with large numbers of 15-40 nm gold nanoparticles (FIG. 2a). The numbers of nanoparticles formed were significantly (approximately 5 fold) higher than that observed in the sap plus chloroauric acid only (FIGS. 1a and 1b), and particles were more uniform. Moreover, TMV also greatly reduced the incidence of aggregation. Low concentrations of TMV were found to have a positive effect on nanoparticle yield and dispersity. Higher concentrations (320 µg/200 µl) led to the production of metallized TMV particles (FIG. 2b) which may also be important for some applications. Therefore, TMV enhances the yield and uniformity of gold nanoparticles in the biosynthesis reactions. In addition TMV is a useful tool for modulating the reactions and can itself can become a template for gold deposition.

Example 2

BPV VLPs Enhances the Yield and Modulates Nanoparticle Particle Shape

Figure 3:
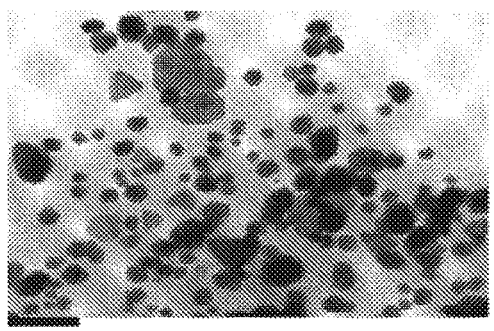
FIG. 3. EM analysis of gold nanoparticles formed after addition of a 10-fold dilution of boiled *N. benthamiana* sap to chloroauric acid ($2.9 \times 10^{-4}$M), in the presence or absence of BPV VLPs. Inclusion of BPV VLPs (8 μg/200 μl) in the reaction mix led to formation of 50-100 nm particles of pentagonal, hexagonal, triangular, spherical, diamond and menhir morphologies.

The experiment of example 1 was repeated, except that Bovine papillomavirus virus-like particles (BPV VLPs) were used in place of TMV. BPV VLPs are composed of just the BPV L1 coat protein, which when expressed in plants self assembles into virus-like particles approximately 30 nm in diameter. These VLPs do not contain nucleic acid and are thus non-infectious. The BPV L1 coat protein gene was cloned into a pCB301 binary expression vector and transferred into *Agrobacterium tumefaciens* strain LBA4404. After overnight growth at 28° C. in LB containing appropriate antibiotics, the *Agrobacterium* was spun down and resuspended in infiltration medium (10 mM Mes, 10 mM $MgCl_2$, 2011M acetosyringone) to an OD 600 of 0.5. The culture was incubated in darkness at room temperature prior to syringe infiltration into *N. benthamiana* leaves. The plants were harvested five days later, allowing sufficient time for significant in planta transient expression of the gene (for an overview of this process see Voinnet et al., 2003 Plant J. 33: 949-956). The leaf material was ground up in liquid nitrogen and extraction of the VLPs was carried out using a modified begomovirus procedure as described by Matic et al. (2012, Plant Biotech Journal 10: 410-421). The integrity of the VLPs was confirmed using EM analysis before being utilized as potential modulators of the synthesis of gold nanoparticles. It was found that addition of 8 µg/200 µl of BPV VLP to the reaction mixture produced a surprisingly diverse array of vast numbers of dispersed nanoparticles ranging in size from 50-150 nm that had pentagonal, hexagonal, triangular, spherical, diamond and menhir morphologies (see FIG. 3) versus aggregates formed in the reaction mix lacking BPV (FIG. 1b). This also contrasts the approximately 5 fold lower yields observed in the reaction mix lacking BPV VLP. Consequently BPV VLPs modulate particle number and shape, when incorporated into the gold nanoparticle synthesis mix.

Example 3

Figure 4:
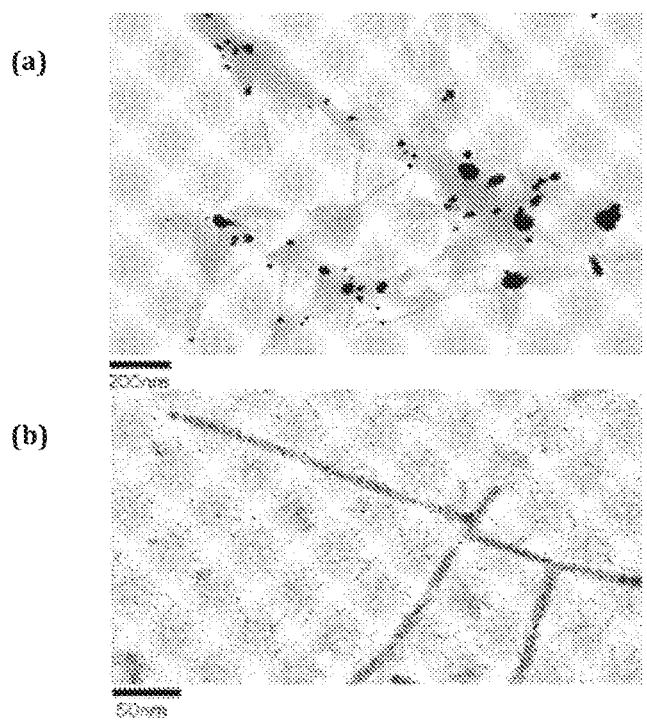
FIG. 4. EM analysis of silver nanoparticles formed after addition of a 10-fold dilution of *N. benthamiana* sap to silver nitrate ($2.5 \times 10^{-4}$M), in the presence TMV (3.2 μg/204.1). (a) Addition of TMV led to formation of dispersed 10-100 nm nanoparticles. (b) TMV particles were metallised.

TMV can Inhibit Aggregation, and Promote Formation of High Yields of Dispersed Silver Nanoparticles, also Acting as a Template for Metallization A 1/10 dilution of sap with $2.5 \times 10^{-4}$M $AgNO_3$ was used instead of HAuC14 in the protocol of example 1. Aggregated concretions of silver nanoparticles of many sizes and shapes (FIG. 1c) were observed in the control lacking TMV. In contrast, the addition of TMV (0.32 µg/200 µl) to the reaction mixture led to the formation of TMV matrices in which dispersed 10-100 nm nanoparticles were observed, with little sign of aggregation (FIG. 4a). Further magnification revealed that the TMV rods were also metallised (FIG. 4b). Therefore TMV can inhibit nanoparticle aggregation, and promote formation of high yields of dispersed nanoparticles, while also acting as a template for metallization.

Example 4

Other Virus-like Particles (VLPs) (such as Potato Leafroll VLPs) as Additives in the Reaction Mix A further embodiment of this technology is the use of other virus-like particles (VLPs) (such as potato leafroll VLPs) as additives in the reaction mix. VLPs are typically composed of the virus coat protein only, and are produced using plant, insect cell, bacterial and mammalian cell expression systems. It has been found that plant and insect cell expression systems can safely and efficiently be used to express virus coat protein monomers to high levels, which then self-assemble into empty virions which do not contain nucleic acid; and are thus safe and non-infectious. Moreover, these VLPs can be further modified by insertion of sequences into regions of the coat protein which are surface exposed. Consequently, the use of VLPs in the plant-based nanoparticle reaction mix will improve safety, and allow further modification of reaction kinetics/dynamics via insertion of sequences into the VLP surface that controls metal or mineral deposition.

The viruses used were BPV virus like particles (VLPs), CPMV VLPs, TMV, PVY according to the examples outlined. Potato leaf roll virus VLPs were not used in any experiments.

Example 5

Reaction Mixes Utilizing Sap Extracts from Monocotyledons Plants; Barley (*Hordeum vulgare*)

The experimental conditions outlined in examples 1-3 were repeated except that barley sap extract was used in place of *N. benthamiana* sap and also that TMV only was investigated. It was found that barley extracts were able to reduce both chloroauric acid and silver nitrate into metallic nanoparticles of similar size and shape to those obtained using *N. benthamiana* extracts. Moreover, it was also observed that inclusion of TMV in the reaction mix inhibited aggregation of metallic nanoparticles and led to the formation of metallised virus.

Figure 5:
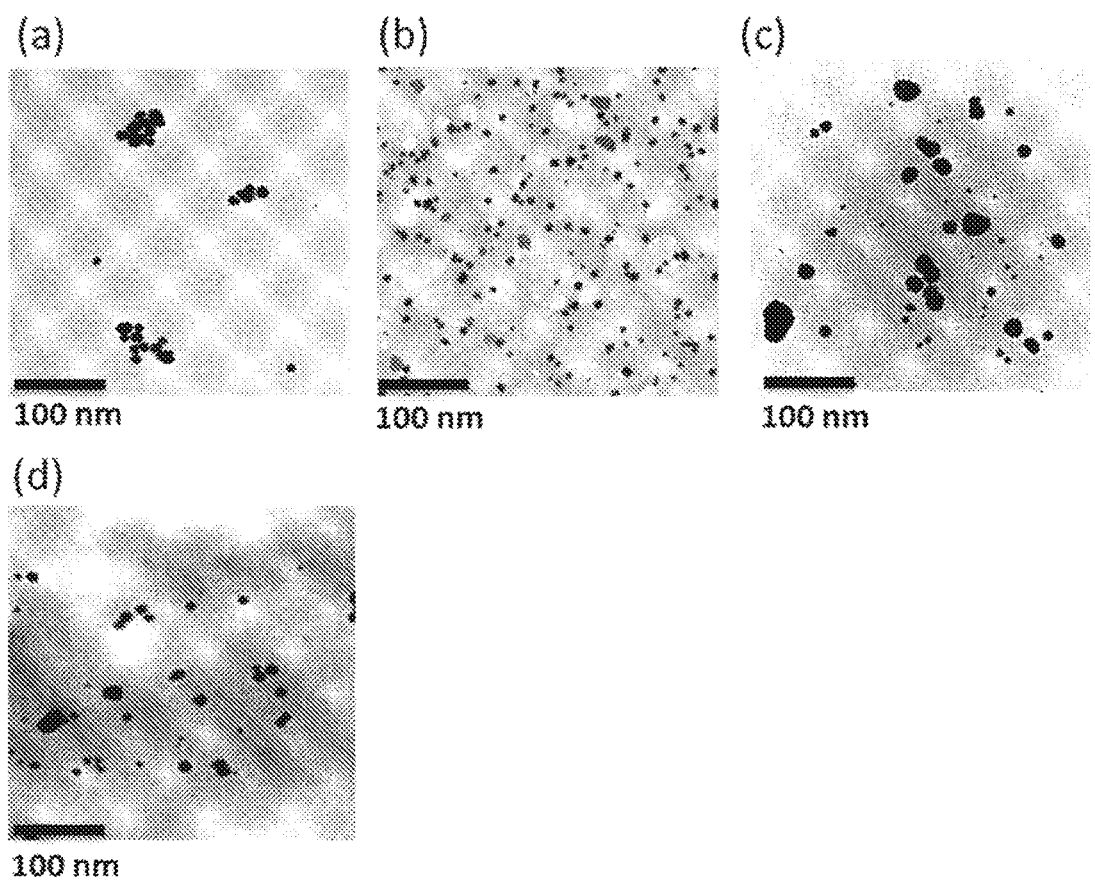
FIG. 5. EM analysis of gold nanoparticles formed after addition of a 50-fold dilution of *H. vulgare* extracts to chloroauric acid ($2.9 \times 10^{-4}$M), in the absence of virus (a) or after the addition of (b) TMV (2 μg/200 μl reaction), (c) PVY (42 μg/200 μl reaction) or (d) eCPMV (175 μg/200 μl reaction).

In particular, the experiment outlined in example 1 was repeated except that *Hordeum vulgare* sap extracts were used in place of *N. benthamiana*. It was found that 50-fold dilutions of the *H. vulgare* extracts mixed with $2.9 \times 10^{-4}$ M HAuC14 led to rapid production of spherical gold nanoparticles in the 10-20 nm size range which were predominantly arranged in aggregates associated with biological material (FIG. 5*a*). Addition of rod-shaped TMV to the reaction mix at a concentration of 2 μg/200 μl reaction significantly enhanced production of 10 nm spherical nanoparticles and inhibited aggregation (FIG. 5*b*). Similar improvements were also obtained when filamentous Potato virus Y (PVY) (FIG. 5*c*) or spherical eCPMV (FIG. 5*d*) were added to the reactions at concentrations of 42 μg/200 μl or 175 μg/200 μl respectively; larger numbers of spherical 10-20 nm nanoparticles and no aggregation was observed when compared to the reactions lacking virus (FIG. 5).

Example 6

Reaction Mixes Utilizing Sap Extracts from Various Plants Such as Blackberries (*Rubus fruticosus*), Cloves (*Syzygium Aromaticum*), Lime (*Citrus aurantifolia*) Fruits, Soybean (*Glycine max*) Leaves and Spinach (*Spinacia oleracea*) Leaves Examples 1-3 are repeated using plant sap from blackberries, cloves, lime fruits, soybean leaves and spinach leaves.

Figure 6:
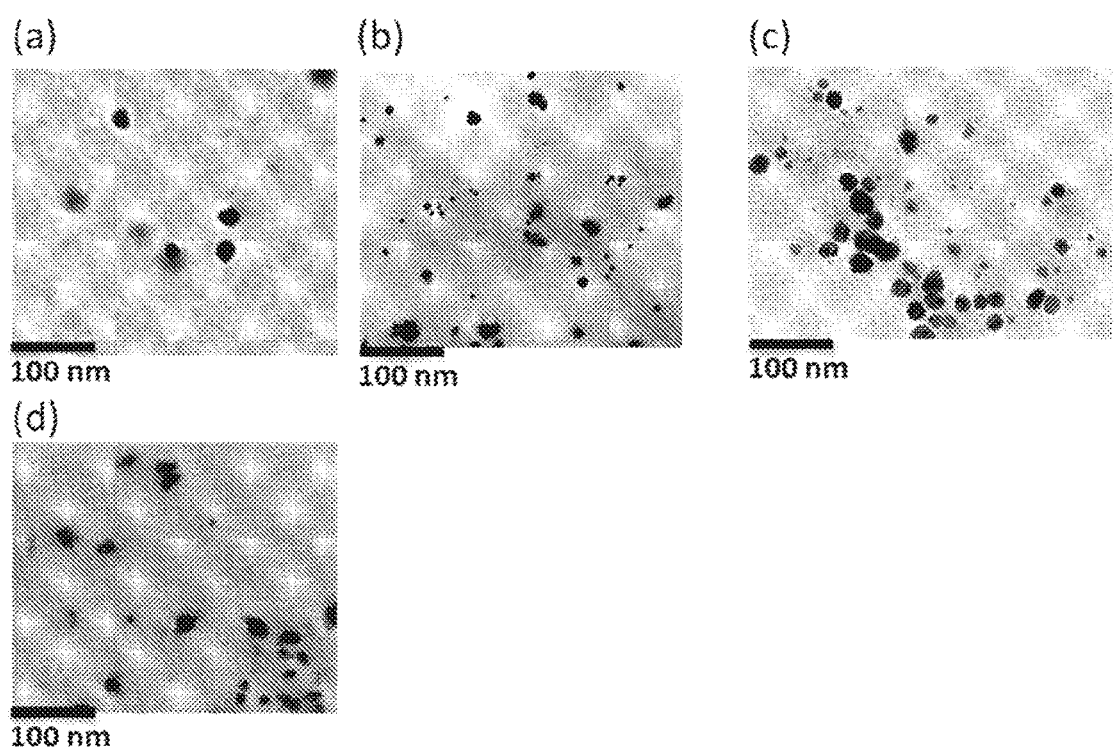
FIG. 6. EM analysis of silver nanoparticles formed after addition of a 50-fold dilution of *H. vulgare* extracts to $2.9 \times 10^{-4}$M $AgNO_3$, in the absence of virus (a) or after the addition of (b) TMV (2 μg/200 μl reaction), (c) PVY (42 μg/200 μl reaction) or (d) eCPMV (175 μg/200 μl reaction).

The experiment outlined in example 5 was repeated except that $2.9 \times 10^{-4}$ M $AgNO_3$ was used in place of $2.9 \times 10^{-4}$ M $HAuCl_4$. It was found that 50-fold dilutions of barley extracts led to the formation of 10-20 nm spherical silver nanoparticles (FIG. 6*a*). In contrast, addition of TMV to the reaction mix at a concentration of 2 μg/200 μl facilitated the increased production of 5-30 nm spherical silver nanoparticles (FIG. 6*b*). The inclusion of PVY at a concentration of 42 μg/200 μl or eCPMV at a concentration of 175 μg/200 μl also led to improvement of the synthesis reaction such that larger numbers 10-25 nm particles were observed than in the reaction without viruses (FIGS. 6*c* and 6*d* respectively).

Example 7

Figure 7:
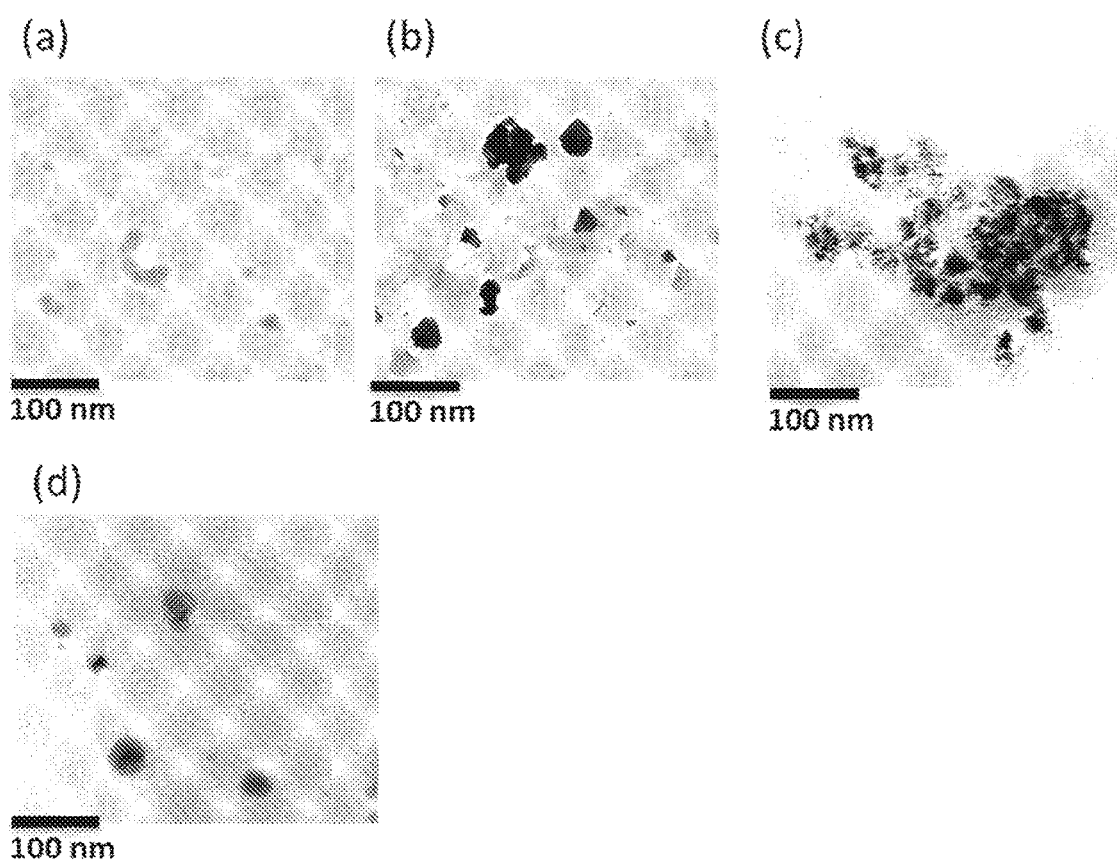
FIG. 7. EM analysis of cobalt nanoparticles formed after addition of neat *H. vulgare* extracts to 0.5 M $Co(NO_3)_2$, in the absence of virus (a) or after the addition of (b) TMV (2 µg/200 µl reaction), (c) PVY (42 µg/200 µl reaction) or (d) eCPMV (175 µg/200 µl reaction).

Inclusion of Spherical, Rod-shaped or Filamentous Viruses Facilitates Production of Cobalt Nanoparticles in *Hordeum vulgare* (Barley) Biosynthesis Reactions The experiment outlined in example 5 was repeated except that neat barley extracts were used in conjunction with 0.5M $Co(NO_3)_2$. It was found that neat barley extracts could not be used to produce cobalt nanoparticles from cobalt salts (FIG. 7*a*). However, addition of TMV to a final concentration of 2 μg/200 μl permitted the production of large 20-50 nm cobalt nanoparticles (FIG. 7*b*). Similarly, nanoparticles of this size were also detected when 175 μg of eCPMV was added to the 200 μl reaction (FIG. 7*d*). In contrast, with PVY (42 μg/200 μl reaction) a large number of 10-30 nm particles were formed in close association (FIG. 7*c*).

Example 8

Figure 8:
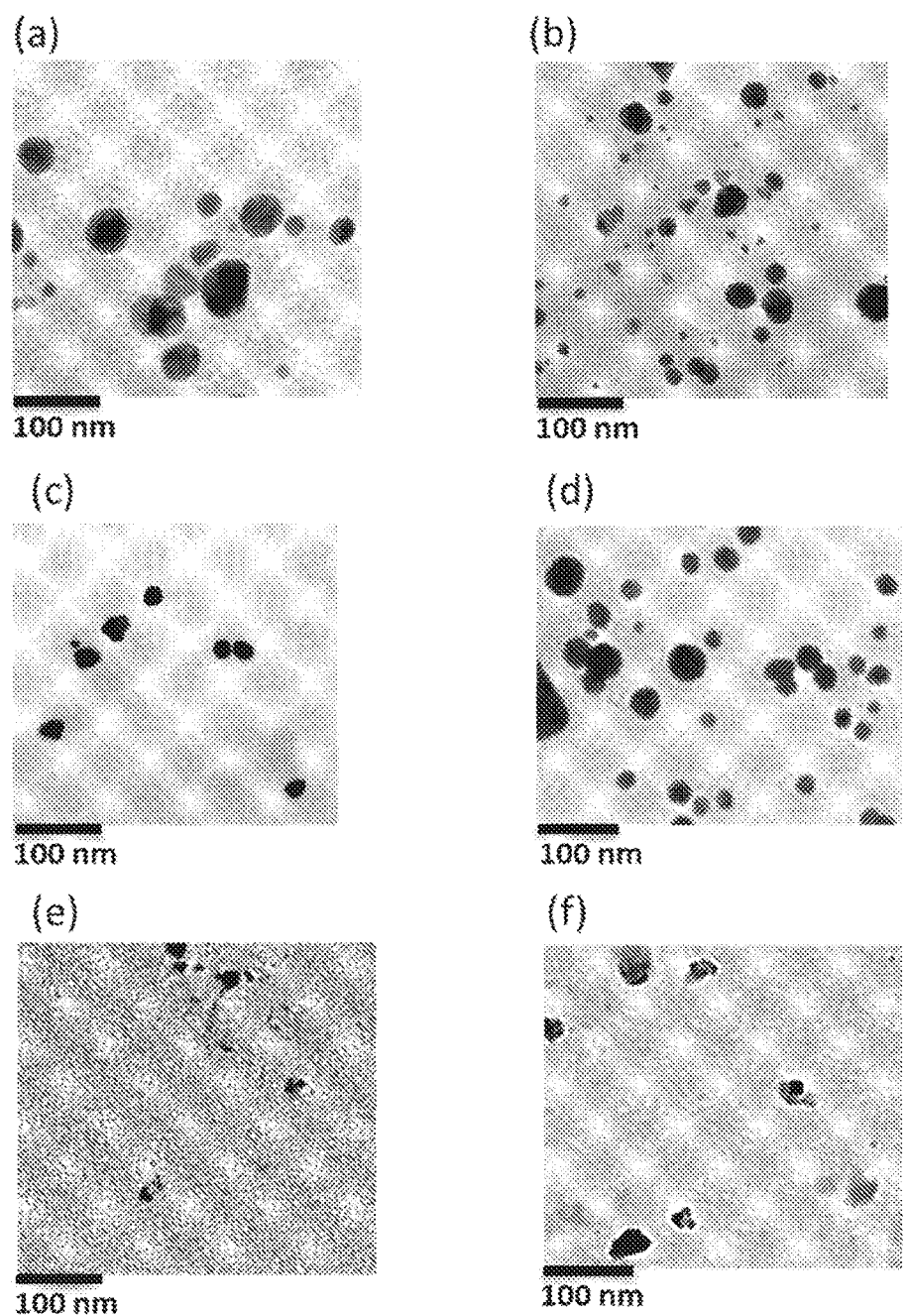
FIG. 8. EM analysis of nanoparticles produced using 10-fold dilutions of *Rubus fruticosus* extracts with (a) 2.9× $10^{-4}$M $HAuCl_4$ only, and with (b) TMV at a final concentration of 0.32 µg/200 µl reaction. (c) silver nanoparticles produced using 10-fold dilution of *Rubus fruticosus* extracts with $2.9 \times 10^{-4}$M $AgNO_3$ only, and with (d) CPMV at a final concentration of 175 µg/200 µl reaction. (e) cobalt nanoparticles produced using neat *Rubus fruticosus* extracts with 0.5 M $Co(NO_3)_2$ only, and with (f) PVY at a concentration of 42 µg/200 µl reaction.

Inclusion of a Rod-shaped Virus Enhances Production of Gold Nanoparticles in *Rubus fruticosus* Extracts It was found that 10-fold dilutions of *Rubus fruticosus* extracts mixed with $2.9 \times 10^{-4}$ M chloroauric acid produced gold nanoparticles in the 5-50 nm size range (FIG. 8*a*). Addition of TMV to a final concentration of 0.32 μg/200 μl enhanced nanoparticle production (FIG. 8*b*) beyond that observed in reactions without virus.

Example 9

Inclusion of a Spherical Virus Enhances and Modifies Production of Silver Nanoparticles in *Rubus fruticosus* Extracts Ten-fold dilutions of *Rubus fruticosus* extracts catalysed the formation of 20 nm silver nanoparticles from $2.9 \times 10^{-4}$ M AgNO$_3$ (FIG. 8c). Addition of eCPMV at a final concentration of 175 μg/200 μl significantly enhanced the numbers of nanoparticles produced and increased their size distribution (FIG. 8d).

Example 10

Inclusion of a Filamentous Virus Facilitates Production of Cobalt Nanoparticles in *Rubus fruticosus* Extracts Ten-fold dilutions of *Rubus fruticosus* extracts were very inefficient at producing cobalt nanoparticles from 0.5M Co(NO$_3$)$_2$ (FIG. 8e). However addition of PVY at a final concentration of 42 μg/200 μl permitted the formation of larger numbers of 30-50 nm nanoparticles (FIG. 8f).

Example 11

Intact Plants Infected with Virus or that Express VLPs from Introduced Nucleic Acid, Grown Hydroponically in Metal Salts for Nanoparticle Production It is considered that a variety of plants that are salt tolerant or are able to hyperaccumulate metal ions, for example *Thellungiella halophila* and *Brassica juncea*, could be grown hydroponically in liquid medium. After infection with virus (such as rod-shaped filamentous and icosahedral viruses) or induction of in planta VLP expression, the plants would be placed into a hydroponic system containing a metal salt/metal acid (such as HAuCl$_4$, KAuCl$_4$, AgNO$_3$, In(OCCH$_3$CHOCCH$_3$)$_3$, PdCl$_2$, H$_2$PtCl$_6$.(H$_2$O) 6 and Ag(NH$_3$)$_2$NO$_3$), at concentrations ranging from 1-10,000 ppm. The plants would uptake the metals and reduce them into nanoparticles. Previous reports have shown that plants infected with viruses often have greatly increased antioxidant levels (Xu et al., 2008 New Phytol 180: 911-921). Moreover, based on our plant-extract based nanoparticle synthesis data, the presence of viruses in the plant may improve numbers and monodispersity of nanoparticles and lead to the formation of metallized viruses.

In an example of this methodology, infection with spherical (Turnip yellow mosaic virus) or filamentous viruses (Turnip mosaic virus) of *Brassica juncea* was undertaken to determine if gold nanoparticle formation was enhanced.

*Brassica juncea* seeds were placed in 1.5 ml eppendorf tubes which were filled with 500 μl of solidified ½ MS (Murashige and Skoog basal salts) pH 5.6, 0.8% agar nutrient media. The eppendorf tubes had their bottoms cut off at the 100 μl graduation mark, to allow penetration of the ½ MS pH5.6 nutrient solution, which was delivered from a reservoir below. The apparatus was designed such that roots would be in darkness and aerial plant parts would be exposed to light. Seeds were stratified overnight at 4° C. before transferring to a greenhouse with 22° C., 16 hour daylength conditions. The reservoir containing the ½ MS pH 5.6, was emptied and replenished every four days. Once plants reached the two true leaf stage of development (i.e two cotyledons plus two true leaves) they were inoculated with either Turnip yellow mosaic virus (TYMV; spherical particles) or Turnip mosaic virus (TuMV; filamentous), whereby crude virus suspensions were mixed with a celite abrasive and rub inoculated onto one of the emergent two true leaves. Two weeks later the symptoms of all the virus inoculated plants became very obvious: leaf malformation, altered coloration and mosaic patterning. At this stage the ½ MS pH 5.6 was removed and the roots were rinsed in water and supplied with either water or 2.9×10$^{-5}$M chloroauric acid. These treatments were applied to virus infected and non-inoculated control plants. Chloroauric acid and water solutions were replenished every two days. Two weeks later, material was harvested from these plants, washed and then dried before grinding into a fine powder for EM analysis.

Figure 9:
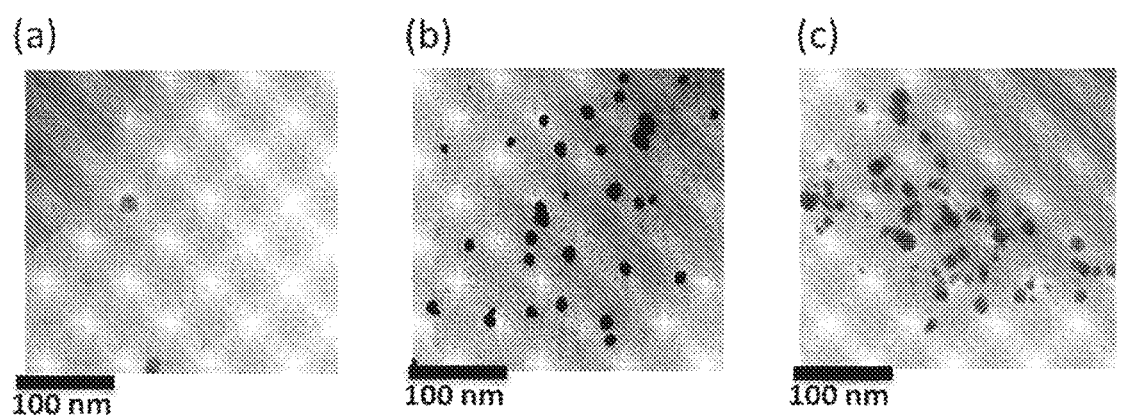
FIG. 9. EM analysis of gold nanoparticles formed in planta after hydroponic application of $2.9 \times 10^{-5}$ M HAuC14 in (a) uninfected plants or (b) TYMV or (c) TuMV infected symptomatic plants.

It was found that in the leaf tissue of chloroauric acid treated uninfected plants that small numbers of 10-20 nm gold nanoparticles were present (FIG. 9a), whereas higher numbers were observed in TYMV (FIG. 9b) and TuMV (FIG. 9c) infected plants. Plant virus infection, therefore enhances the formation and accumulation of gold nanoparticles in whole plants.

Example 12

Figure 10:
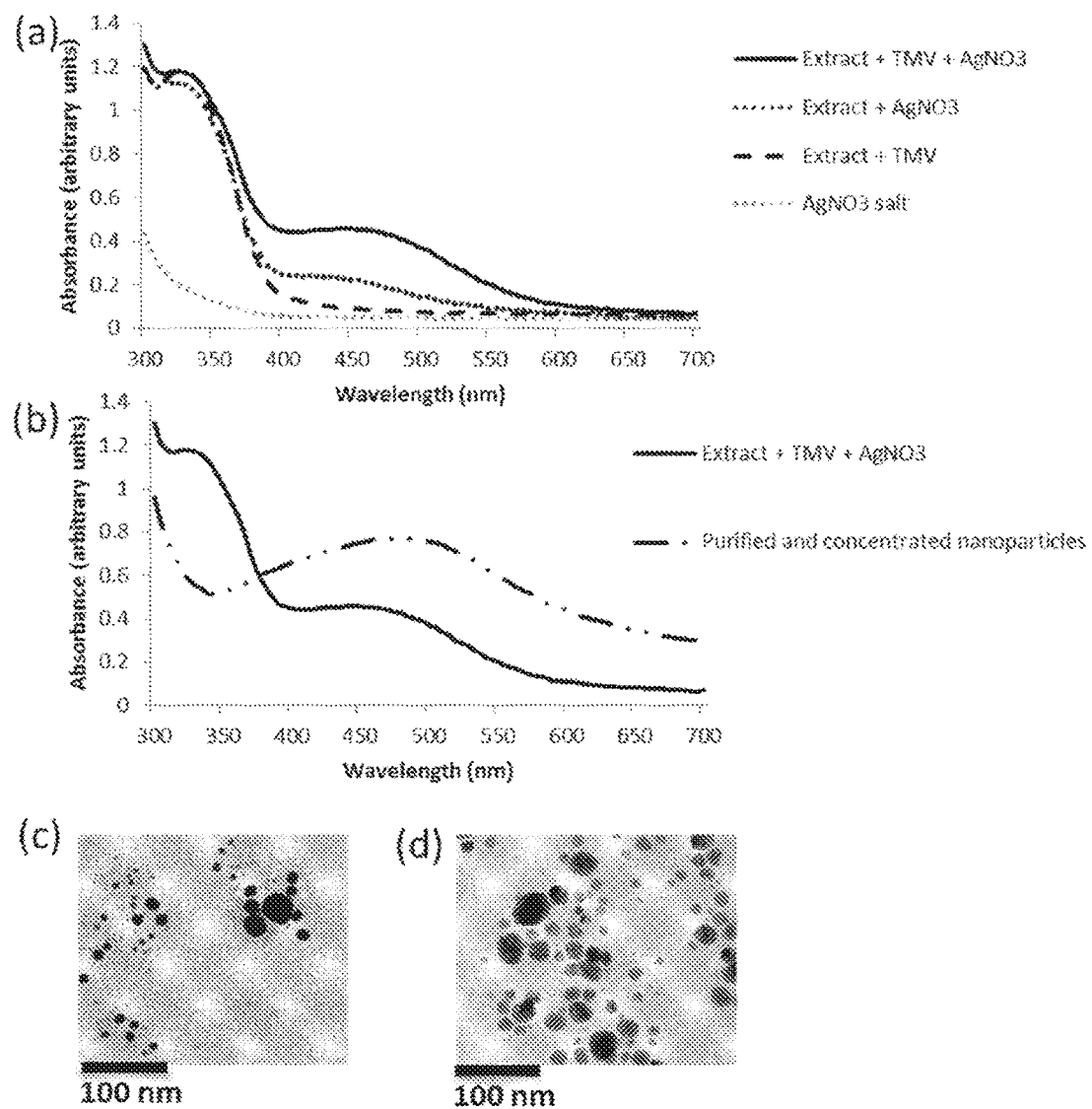
FIG. 10. UV-visible light spectrophotometry on silver nanoparticles produced using 10-fold dilution of barley extracts with $2.9 \times 10^{-4}$ M $AgNO_3$ in the presence or absence of 100 µg/ml TMV. The presence of silver nanoparticles is indicated by peak at around 475 nm and the broad shoulders from 350 nm to 600 nm, which may vary as a function of nanoparticle size. (a) Shows spectra from reactions consisting of salt only, extract with TMV, extract with $AgNO_3$, and extract with $AgNO_3$ and TMV. TMV only was not shown since the low concentrations used in the reactions precludes detection using this analytical method. (b) Shows the effect on nanoparticle yield and purity by purifying using two centrifugation and washing steps and a concentration step (nanoparticles were concentrated 3-fold by resuspending the pellet in a third of the original supernatant volume); most contaminants were removed (see 300-350 region) and yield enhanced. (c) EM analysis of nanoparticles before purification and concentration, and afterwards (d).

Nanoparticles can be Purified from Plant Extract Synthesis Reactions and Concentrated 10 ml silver nanoparticle reactions were set up by combining a 1/10 dilution of barley extracts with 2.9×10$^{-4}$M AgNO$_3$ in the presence or absence of 100 μl/ml TMV. The reactions were left for 24 hours to allow them to progress to completion and facilitate the sedimentation of large aggregates. The supernatants were taken and analysed using spectrophotometry to determine the formation of silver nanoparticles (FIG. 10a). The presence of silver nanoparticles in the reaction can be determined due to a characteristic spectral trace: a peak at 450-470 nm wavelengths with broad shoulders stretching from 350 nm to 600 nm. This peak was detected in the extract plus silver salt reaction, indicating the presence of nanoparticles (FIG. 10a). As expected, addition of TMV to this reaction significantly enhanced the magnitude of this peak (FIG. 10a), which indicates increased nanoparticle production; which is consistent with our previous findings. As expected, AgNO$_3$ only or extract with TMV only did not produce the typical silver nanoparticle curve, due to the absence of nanoparticles (FIG. 10a). Spectra of TMV only and extract only are not shown since the low concentration of TMV in the reaction mixes precludes detection using spectrophotometric approaches, such that the spectra of the extract only is equivalent to that of extract plus virus only. For subsequent purification and concentration of the silver nanoparticles from the extract with TMV, 9 ml of supernatant was collected and centrifuged for 10 minutes at 13,000 g. The supernatants were discarded and the pellets were resuspended in distilled deionized water to the original volume. Two further centrifugation/resuspension steps were carried out, with the final resuspension step involving addition of 3 ml of water, effectively theoretically concentrating the nanoparticles three-fold. Subsequent UV-visible spectrophotometric analysis confirmed that the purification and concentration of the nanoparticles was successful: the expected nanoparticle peak was higher and many contaminants were removed (see the decrease in the 300-350 nm region; FIG. 10b) when compared to the starting supernatant. By integrating the area under the curves (in FIG. 10b) between 375 and 600 nm wavelengths, it was estimated that the purification and concentration method led to a 2.6-fold enrichment in nanoparticle yield. By comparing the theoretical and actual fold enrichment we can estimate that ~86% of the nanoparticles are retained during the purification procedure. FIGS. 10c and d respectively show EM analysis of silver nanoparticles before and after purification and concentration. As expected, greater numbers of nanoparticles were observed after concentration (FIG. 10c and d). Thus metal nanoparticles can be purified and concentrated from plant extract reactions using simple low speed centrifugation and washing steps.

Although the invention has been particularly shown and described with reference to particular examples, it will be understood by those skilled in the art that various changes in the form and details may be made therein without departing from the scope of the present invention.

REFERENCES

Hoeppener C and Novotny L. (2012) Quarterly reviews of Biophys 45: 209-255.
Wang, J. (2012) Microchimia Acta 117: 245-270.
Narayanan K B, Sakthivel N. (2011) Adv Colloid Interface Sci 169:59-79.
Raveendran P, Fu J, Wallen S L. (2003) J Am Chem Soc 125:13940.
Sharma V K, Yngard R A, Lin Y. (2009) J Colloid Interface Sci 145:83.
Narayanan K B, Sakthivel N. (2010) J Colloid Interface Sci 156:1.
Govindaraju K, Basha S K, Kumar V G, Singaravelu G. (2008) J Mater Sci 43:5115.
Scarano G, Morelli E. (2002) Biometals 15:145.
Scarano G, Morelli E. (2003) Plant Sci 165:803.
Anshup, Venkataraman J S, Subramaniam C, Kumar R R, Priya S, Kumar T R S, et al. (2005) Langmuir 21:11562.
Lengke F M, Fleet E M, Southam G. (2007). Langmuir 23:2694-2699.
Shankar S S, Ahmad A, Pasricha R, Sastry M. (2003) J Mater Chem13:1822 Shankar S S, Rai A, Ankamwar B, Singh A, Ahmad A, Sastry M. (2004) Nat Mater 3: 482.
Shankar S S, Rai A, Ahmad A, Sastry M. (2004b) J Colloid Interface Sci 275:496. Maensiri S, Laokul P, Klinkaewnarong J, Phokha S, Promarak V, Seraphin S. (2008) J Optoelectron Adv Mater 10:161.
Vilchis-Nestor A R, Sanchez-Mendieta V, Camacho-Lopez M A, Gomez-Espinosa R M, Camacho-Lopez M A, Arenas-Alatorre J A. (2008) Mater Lett 62:3103.
Song J Y, Jang H K, Kim B S. (2009) Proc Biochem 44:1133.
Song J Y, Kim B S. (2009) Bioprocess Biosyst Eng 32:79.
Kadri A, Maiss E, Amsharov N, Bittner A M, Balci S, Kern K, Jeske H, Wege C. (2011) Virus Research 157:35-46.
Aljabali A A A, Barclay J E, Lomonossoff G P, Evans D J. (2010) Nanoscale 2, 2596-2600.
Balci, S, Hahn, K, Kopold, P, Kadri, A, Wege, C, Kern, K, and Bittner, A M. (2012) Nanotechnology 23.
Knez M, Kadri A, Wege C, Gosele U, Jeske H, and Nielsch K. (2006) Nano Lett. 6, 1172-1177.
Endo M, Wang H X, Fujitsuka M, and Majima T. (2006) Chemistry 12, 3735-3740.
Shimizu T, Masuda M, and Minamikawa H. (2005). Chem Rev. 105, 1401-1443.
Lee S Y, Lim J S, and Harris M T. (2012) Biotechnol. Bioeng. 109, 16-30.
Bittner A M. (2005) Naturwissenschaften 92, 51-64.
Dujardin E, Peet C, Stubbs G, Culver J N, and Mann S. (2003) Nano Lett 3, 413-417.
Atanasova P, Rothenstein D, Schneider J J, Hoffmann R C, Dilfer S, Eiben S, Wege C, Jeske H, and Bill J. (2011) Adv. Mater. 23, 4918-4922.
Chen X L, Gerasopoulos K, Guo J C, Brown A, Ghodssi R, Culver J N, and Wang C S. (2011) Electrochim. Acta 56, 5210-5213.
Wu Z, Mueller A, Degenhard S, Ruff S E, Geiger F, Bittner A M, Wege C, and Krill C E. (2010). ACS Nano 4, 4531-8.
Love, A. J., Chapman, S. N., Matic, S., Noris, E., Lomonossoff, G. P., Taliansky, M. In planta production of a candidate vaccine against bovine papillomavirus type 1. 2012. Planta. 236(4), 1305-13.
Tan, N. T., Lee, Y., Wang, D. I. C. Uncovering the design rules for peptide synthesis of metal nanoparticles. 2010. J. Am. Chem. Soc. 132, 5677-5686.
Saunders, K., Sainsbury, F., Lomonossoff, G. P. 2009. Efficient generation of Cowpea mosaic virus empty virus-like particles by the proteolytic processing of precursors in insect cells and plants. Virology, 353, 329-337.
Aljabali, A. A. A., Shah, S. N., Evans-Gowing, R., Lomonossoff, G. P., Evans, D. J. 2011.
Chemically-coupled-peptide-promoted virus nanoparticle templated Mineralization. Integr. Biol., 2011, 3, 119-125.
Lukman A I, Gong B, Marjo C E, Roessner U, Harris A T. (2011) J. Colloid Interface Sci 353:433-444.
Lin L, Wang W, Huang J, Li Q Sun D, Yang X, Wang H, He N, Wang Y. (2010) Chem Eng J 162: 852-858.
Das R K, Gogoi N, Bora U. (2011) Bioprocess Biosyst Eng 34: 615-619.
Thuenemann E V, Lenzi P, Love A J, Taliansky M E, Becares M, Zuniga S, Enjuanes L, Zahmanova G G, Minkov I N, Matic S, Noris E, Meyers A, Hattingh A, Rybicki E P, Kiselev O I, Ravin N V, Eldarov M A, Skryabin K G, Lomonossoff G P. (2013). Curr Pharma Design 19:5564-5573.
Nadagouda M N, Varma R S. (2008). Green Chem 10:859-862.
Nadagouda M N, Castle A B, Murdock R C, Hussain S M, Varma R S. (2010). Green Chem 12:114-122.
Njagi E C, mHuang H, Stafford L, Genuino H, Galindo H M, Collins J B, Hoag G E, Suib S L. (2010). Langmuir 27:264-271.

The invention claimed is:

1. A process for producing an enhanced yield and monodispersity of metal-coated virus particles or metallic nanoparticles, said process comprising:
    (a) admixing virus particles, plant material with reducing power, and a metal salt;
    (b) reducing a metal ion of the metal salts using the plant material; and
    (c) forming the metal-coated virus particles or metallic nanoparticles.

2. The process as claimed by claim 1, wherein the virus particles are selected from non-enveloped virus particle having a capsid coat, bacteriophages and virus-like particles which lack nucleic acid content.

3. The process as claimed by claim 2, wherein the non-enveloped viruses have a capsid coat selected from a helical capsid, a filamentous capsid, and icosahedral capsid and the bacteriophages have a morphology selected from isometric, lemon-shaped, ovoid, bottle-shaped, rod-shaped, filamentous, and pleomorphic.

4. The process as claimed by claim 1, wherein the virus particles are genetically and/or chemically modified viruses with an altered surface which displays metal binding or reducing peptides.

5. The process as claimed by claim 1, wherein the plant material is plant sap obtained from plant material selected from leaves and stalk.

6. The process as claimed by claim 1, wherein the plant material is provided by a dicotyledonous or monocotyledonous plant.

7. The process as claimed by claim 1, wherein the metal salts are selected from transition metals and aluminium, gallium, germanium, tin, silver, gold, iron, copper, indium, platinum, palladium, rhodium, iridium, cobalt.

8. The process as claimed by claim 1, wherein the metal salt is provided as a metal chelate or metal acid.

9. The process as claimed by claim 1, wherein the plant material is extracted from *Nicotiana* sp., *Musa* sp., *Psidium* sp., *Avena* sp., *Azadirachta* sp., *Chenopodium* sp., *Syzygium* sp., *Citrus* sp., *Glycine* sp., *Spinacia* sp., *Carica* sp., *Stevia* sp., *Pinus* sp., *Diopyros* sp., *Gingko* sp., *Magnolia* sp., *Platanus* sp., *Nicotiana benthamiana, Musa pradisiaca, Psidium guava, Avena sativa, Azadirachta indica, Chenopodium album, Syzygium aromaticum, Citrus, Glycine max, Spinacia oleracea, Hordeum vulgare, Triticum* spp, *Zea mays, Oryza sativa, Solanum tuberosum, Daucus carota, Brassica* spp, *Beta vulgaris , Saccharum, Solanum lycopersicum* or *Vitis*.

10. The process as claimed by claim 1, wherein a first metal salt is admixed to the plant material and virus particle at a first time point and a second or subsequent metal salt is admixed at a second time point.

11. The process as claimed by claim 1, wherein the metal salt is provided at a concentration in the range 1M to $1 \times 10^{-5}$M.

12. The process as claimed by claim 1, wherein the process is conducted ex planta.

13. The process as claimed by claim 1, wherein the process is conducted in planta.

14. The process as claimed by claim 13, wherein the process comprises:
   i) providing a plant infected with a non-enveloped virus and/or able to express a non-enveloped virus particle; and
   ii) exposing said plant to a concentration of a water-soluble metal salt sufficient for nanoparticle formation.

15. The process as claimed by claim 1, wherein the process comprises:
   i) providing a plant and exposing said plant to a concentration of a water-soluble metal salt sufficient for nanoparticle formation; and
   ii) exposing said plant to a non-enveloped virus and/or a genetic construct able to express a non-enveloped virus particle.

16. The process as claimed by claim 1, wherein the plant material has the capacity to reduce metals with reduction potentials in the range 1.5 V to −0.44 V.

17. A metal-coated virus particle or metallic nanoparticle produced by the process of claim 1.

18. The metal-coated virus particle or metallic nanoparticle as claimed in claim 17 sized between 5 nm to 100 nm.

19. A structure formed by metal-coated virus particles or metallic nanoparticles as claimed by claim 17.

20. A device comprising a metal-coated virus particle or metallic nanoparticle as claimed by claim 17.

\* \* \* \* \*